(12) United States Patent
Kleiner

(10) Patent No.: US 9,060,877 B2
(45) Date of Patent: Jun. 23, 2015

(54) FUSION CAGE WITH COMBINED BIOLOGICAL DELIVERY SYSTEM

(75) Inventor: Jeffrey Kleiner, Aurora, CO (US)

(73) Assignee: Spinal Surgical Strategies, LLC, Denver, CO (US)

( * ) Notice: Subject to any disclaimer, the term of this patent is extended or adjusted under 35 U.S.C. 154(b) by 0 days.

(21) Appl. No.: 13/367,295

(22) Filed: Feb. 6, 2012

(65) Prior Publication Data

US 2012/0136442 A1    May 31, 2012

Related U.S. Application Data

(63) Continuation-in-part of application No. 12/886,452, filed on Sep. 20, 2010, now Pat. No. 8,906,028.

(60) Provisional application No. 61/243,664, filed on Sep. 18, 2009, provisional application No. 61/439,712, filed on Feb. 4, 2011.

(51) Int. Cl.
*A61F 2/46* (2006.01)
*A61F 2/44* (2006.01)
(Continued)

(52) U.S. Cl.
CPC ............ *A61F 2/4601* (2013.01); *A61B 17/8802* (2013.01); *A61F 2/442* (2013.01); *A61F 2/4455* (2013.01); *A61F 2/4611* (2013.01); *A61F 2002/30153* (2013.01); *A61F 2002/30601* (2013.01); *A61F 2002/30828* (2013.01); *A61F 2002/4475* (2013.01); *A61F 2002/4602* (2013.01); *A61F 2002/4627* (2013.01); *A61F 2/30767* (2013.01); *A61F 2/447* (2013.01); *A61F 2002/2817* (2013.01); *A61F 2002/2835* (2013.01); *A61F 2002/3071* (2013.01);

(Continued)

(58) Field of Classification Search
USPC ........... 606/92–94; 623/17.11, 17.16; 604/15, 604/57, 187, 218, 231
See application file for complete search history.

(56) References Cited

U.S. PATENT DOCUMENTS

| D30,951 S | 6/1899 | Saint Cyr, Jr. |
|---|---|---|
| 1,867,624 A | 7/1932 | Hoffman |

(Continued)

FOREIGN PATENT DOCUMENTS

| FR | 2790946 | 9/2000 |
|---|---|---|
| WO | WO 99/08627 | 2/1999 |

(Continued)

OTHER PUBLICATIONS

U.S. Appl. No. 13/168,611, filed Jun. 24, 2011, Kleiner.

(Continued)

*Primary Examiner* — Christian Sevilla
(74) *Attorney, Agent, or Firm* — Sheridan Ross P.C.

(57) ABSTRACT

The present invention relates to an apparatus and method for near-simultaneous and integrated delivery of bone graft material during the placement of surgical cages or other medical implants in a patient's spine. The integrated fusion cage and graft delivery device according to various embodiments delivers and disperses biologic material through a fusion cage to a disc space and, without withdrawal from the surgical site, may selectably detach the fusion cage for deposit to the same disc space. The integrated fusion cage and graft delivery device is formed such that a hollow tube and plunger selectively and controllably place bone graft material and a fusion cage in or adjacent to the bone graft receiving area.

20 Claims, 13 Drawing Sheets

(51) Int. Cl.
  *A61B 17/56* (2006.01)
  *A61B 17/88* (2006.01)
  *A61F 2/30* (2006.01)
  *A61F 2/28* (2006.01)

(52) U.S. Cl.
  CPC .............. *A61F2002/30785* (2013.01); *A61F 2002/30878* (2013.01); *A61F 2002/30904* (2013.01); *A61F 2002/469* (2013.01); *A61F 2002/4693* (2013.01); *A61F 2002/4694* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01)

(56) References Cited

U.S. PATENT DOCUMENTS

| | | |
|---|---|---|
| 2,520,464 A | 8/1950 | Hubner |
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A * | 7/1981 | Solomon ............... 366/139 |
| 4,338,925 A | 7/1982 | Miller |
| 4,430,062 A | 2/1984 | Henrichsen et al. |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,743,256 A | 5/1988 | Brantigan |
| 4,877,399 A | 10/1989 | Frank et al. |
| 4,925,924 A | 5/1990 | Silver et al. |
| D309,499 S | 7/1990 | Bowman et al. |
| D312,309 S | 11/1990 | Michelson |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| D351,022 S | 9/1994 | Saito |
| 5,354,292 A | 10/1994 | Braeuer et al. |
| 5,395,372 A | 3/1995 | Holt et al. |
| 5,425,772 A * | 6/1995 | Brantigan ............... 623/17.11 |
| D360,689 S | 7/1995 | Giampapa |
| 5,431,658 A | 7/1995 | Moskovich |
| 5,443,514 A | 8/1995 | Steffee |
| D364,462 S | 11/1995 | Michelson |
| 5,520,611 A | 5/1996 | Rao et al. |
| D370,531 S | 6/1996 | Ash et al. |
| 5,527,312 A | 6/1996 | Ray |
| D372,311 S | 7/1996 | Koros et al. |
| 5,531,749 A | 7/1996 | Michelson |
| 5,541,191 A | 7/1996 | Skotnicki et al. |
| D372,781 S | 8/1996 | Reif |
| 5,549,607 A | 8/1996 | Olson et al. |
| 5,554,191 A | 9/1996 | Lahille et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,655 A | 9/1997 | Laboureau et al. |
| 5,665,122 A | 9/1997 | Kambin |
| 5,683,464 A | 11/1997 | Wagner et al. |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| 5,741,253 A | 4/1998 | Michelson |
| 5,762,629 A | 6/1998 | Kambin |
| 5,779,642 A | 7/1998 | Nightengale |
| 5,782,919 A | 7/1998 | Zdeblick et al. |
| 5,797,918 A | 8/1998 | McGuire et al. |
| 5,836,948 A | 11/1998 | Zucherman et al. |
| 5,836,958 A | 11/1998 | Ralph |
| 5,860,973 A | 1/1999 | Michelson |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,904,718 A | 5/1999 | Jefferies |
| 5,906,616 A | 5/1999 | Pavlov et al. |
| 5,925,051 A | 7/1999 | Mikhail |
| 5,925,056 A | 7/1999 | Thomas et al. |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,989,257 A | 11/1999 | Tidwell et al. |
| 5,997,895 A | 12/1999 | Narotam et al. |
| 6,004,191 A | 12/1999 | Schur et al. |
| 6,004,326 A | 12/1999 | Castro et al. |
| 6,013,028 A | 1/2000 | Jho et al. |
| 6,019,765 A * | 2/2000 | Thornhill et al. ............. 606/94 |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,059,829 A | 5/2000 | Schlapfer et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,123,705 A | 9/2000 | Michelson |
| 6,136,001 A | 10/2000 | Michelson |
| 6,142,998 A | 11/2000 | Smith et al. |
| 6,146,420 A | 11/2000 | McKay |
| 6,149,096 A | 11/2000 | Hartley |
| 6,152,871 A | 11/2000 | Foley et al. |
| 6,159,211 A | 12/2000 | Boriani et al. |
| 6,159,245 A | 12/2000 | Meriwether et al. |
| 6,180,085 B1 | 1/2001 | Achilefu |
| 6,200,322 B1 | 3/2001 | Branch et al. |
| 6,209,886 B1 | 4/2001 | Estes et al. |
| 6,216,573 B1 | 4/2001 | Moutafis et al. |
| 6,224,599 B1 | 5/2001 | Baynham et al. |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,290,724 B1 | 9/2001 | Marino |
| 6,299,613 B1 | 10/2001 | Ogilvie et al. |

(56) References Cited

U.S. PATENT DOCUMENTS

| | | |
|---|---|---|
| 6,309,395 B1 | 10/2001 | Smith et al. |
| 6,325,805 B1 | 12/2001 | Ogilvie et al. |
| 6,328,738 B1 | 12/2001 | Suddaby |
| 6,336,928 B1 | 1/2002 | Guerin et al. |
| 6,342,074 B1 | 1/2002 | Simpson |
| 6,364,880 B1 | 4/2002 | Michelson |
| 6,375,635 B1 | 4/2002 | Moutafis et al. |
| 6,387,096 B1 | 5/2002 | Hyde, Jr. |
| 6,409,765 B1 | 6/2002 | Bianchi et al. |
| 6,436,101 B1 | 8/2002 | Hamada |
| 6,451,017 B1 | 9/2002 | Moutafis et al. |
| 6,454,806 B1 | 9/2002 | Cohen et al. |
| 6,467,556 B2 | 10/2002 | Alsruhe |
| D467,657 S | 12/2002 | Scribner |
| 6,500,206 B1 | 12/2002 | Bryan |
| 6,511,493 B1 | 1/2003 | Moutafis et al. |
| D469,871 S | 2/2003 | Sand |
| 6,520,976 B1 | 2/2003 | Gage |
| 6,524,318 B1 | 2/2003 | Longhini et al. |
| 6,565,574 B2 | 5/2003 | Michelson |
| 6,569,201 B2 | 5/2003 | Moumene et al. |
| 6,613,091 B1 | 9/2003 | Zdeblick et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,695,882 B2 | 2/2004 | Bianchi et al. |
| 6,699,288 B2 | 3/2004 | Moret |
| 6,709,438 B2 | 3/2004 | Dixon et al. |
| 6,719,760 B2 | 4/2004 | Dorchak et al. |
| 6,719,795 B1 | 4/2004 | Cornwall et al. |
| 6,730,125 B1 | 5/2004 | Lin |
| 6,743,257 B2 | 6/2004 | Castro |
| 6,746,487 B2 | 6/2004 | Scifert et al. |
| 6,764,491 B2 | 7/2004 | Frey et al. |
| 6,770,074 B2 | 8/2004 | Michelson |
| 6,773,437 B2 | 8/2004 | Ogilvie et al. |
| 6,800,093 B2 | 10/2004 | Nicholson et al. |
| 6,824,565 B2 | 11/2004 | Muhanna et al. |
| 6,830,574 B2 | 12/2004 | Heckele et al. |
| 6,852,126 B2 | 2/2005 | Ahlgren |
| 6,869,430 B2 * | 3/2005 | Balbierz et al. ............ 606/41 |
| 6,890,728 B2 | 5/2005 | Dolecek et al. |
| 6,899,712 B2 | 5/2005 | Moutafis et al. |
| 6,923,792 B2 | 8/2005 | Staid et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,974,480 B2 | 12/2005 | Messerli et al. |
| 6,991,653 B2 | 1/2006 | White et al. |
| 6,994,728 B2 | 2/2006 | Zubok et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |
| 7,025,769 B1 | 4/2006 | Ferree |
| 7,033,317 B2 | 4/2006 | Pruitt |
| 7,041,136 B2 | 5/2006 | Goble et al. |
| 7,066,961 B2 | 6/2006 | Hichelson |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,128,760 B2 | 10/2006 | Michelson |
| 7,135,043 B2 | 11/2006 | Nakahara et al. |
| 7,182,782 B2 | 2/2007 | Kirschman |
| 7,204,825 B2 | 4/2007 | Cimino et al. |
| 7,207,992 B2 | 4/2007 | Ritland |
| 7,211,112 B2 | 5/2007 | Baynham et al. |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,288,093 B2 | 10/2007 | Michelson |
| 7,316,070 B2 | 1/2008 | Green |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,421,772 B2 | 9/2008 | Gao et al. |
| 7,429,270 B2 | 9/2008 | Baumgartner et al. |
| D579,562 S | 10/2008 | Anderson et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| D582,552 S | 12/2008 | Berberich |
| 7,461,803 B2 | 12/2008 | Boerner |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D590,945 S | 4/2009 | Berberich |
| 7,513,901 B2 | 4/2009 | Scifert et al. |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| D594,119 S | 6/2009 | Berberich et al. |
| 7,553,320 B2 | 6/2009 | Molz, IV et al. |
| D597,669 S | 8/2009 | Petersen |
| D598,096 S | 8/2009 | Petersen |
| D599,015 S | 8/2009 | Petersen |
| 7,578,820 B2 | 8/2009 | Moore et al. |
| D600,806 S | 9/2009 | Horton et al. |
| D601,251 S | 9/2009 | Horton et al. |
| 7,582,058 B1 | 9/2009 | Miles et al. |
| 7,582,107 B2 | 9/2009 | Trail et al. |
| 7,595,043 B2 | 9/2009 | Hedrick et al. |
| D603,502 S | 11/2009 | Petersen |
| 7,615,078 B2 | 11/2009 | White et al. |
| 7,618,423 B1 | 11/2009 | Valentine et al. |
| 7,625,374 B2 | 12/2009 | Branch et al. |
| 7,632,276 B2 | 12/2009 | Fishbein |
| D608,001 S | 1/2010 | Reardon et al. |
| 7,655,027 B2 | 2/2010 | Michelson |
| 7,658,766 B2 | 2/2010 | Melkent et al. |
| 7,671,014 B2 | 3/2010 | Beals et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,699,852 B2 | 4/2010 | Frankel et al. |
| 7,708,761 B2 | 5/2010 | Petersen |

(56) References Cited

U.S. PATENT DOCUMENTS

| | | |
|---|---|---|
| 7,717,685 B2 | 5/2010 | Moutafis et al. |
| 7,722,530 B2 | 5/2010 | Davison |
| 7,722,613 B2 | 5/2010 | Sutterlin et al. |
| 7,723,291 B2 | 5/2010 | Beals et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| D620,108 S | 7/2010 | Eitenmueller et al. |
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Iott et al. |
| 7,758,644 B2 | 7/2010 | Trieu |
| 7,758,648 B2 | 7/2010 | Castleman et al. |
| 7,763,025 B2 | 7/2010 | Assell et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| 7,819,921 B2 | 10/2010 | Grotz |
| D627,460 S | 11/2010 | Horton |
| 7,824,328 B2 | 11/2010 | Gattani et al. |
| 7,824,332 B2 | 11/2010 | Fakhrai |
| 7,824,410 B2 | 11/2010 | Simonson |
| 7,824,703 B2 | 11/2010 | Scifert et al. |
| 7,828,804 B2 | 11/2010 | Li et al. |
| 7,828,845 B2 | 11/2010 | Estes et al. |
| 7,828,849 B2 | 11/2010 | Lim |
| 7,837,713 B2 | 11/2010 | Petersen |
| 7,837,732 B2 | 11/2010 | Zucherman et al. |
| D628,694 S | 12/2010 | Donnez |
| D629,896 S | 12/2010 | Horton |
| 7,846,210 B2 | 12/2010 | Perez-Cruet et al. |
| 7,850,733 B2 | 12/2010 | Baynham et al. |
| 7,850,735 B2 | 12/2010 | Eisermann et al. |
| 7,850,736 B2 | 12/2010 | Heinz et al. |
| D631,156 S | 1/2011 | Halder et al. |
| 7,867,277 B1 | 1/2011 | Tohmeh |
| 7,897,164 B2 | 3/2011 | Scifert |
| 7,897,564 B2 | 3/2011 | Beals et al. |
| 7,905,840 B2 | 3/2011 | Pimenta et al. |
| 7,905,886 B1 | 3/2011 | Curran et al. |
| 7,918,891 B1 | 4/2011 | Curran et al. |
| 7,922,766 B2 | 4/2011 | Grob et al. |
| 7,927,361 B2 | 4/2011 | Oliver et al. |
| D637,721 S | 5/2011 | Horton |
| 7,935,124 B2 | 5/2011 | Frey et al. |
| 7,938,857 B2 | 5/2011 | Garcia-Bengochea et al. |
| 7,939,092 B2 | 5/2011 | McKay et al. |
| 7,951,107 B2 | 5/2011 | Staid et al. |
| 7,964,208 B2 | 6/2011 | Spagnoli et al. |
| D641,872 S | 7/2011 | Solingen et al. |
| D641,873 S | 7/2011 | Solingen et al. |
| D641,874 S | 7/2011 | Solingen et al. |
| D642,268 S | 7/2011 | Qureshi |
| 7,985,256 B2 | 7/2011 | Grotz et al. |
| D643,921 S | 8/2011 | Davila |
| D647,202 S | 10/2011 | Scifert |
| 8,080,521 B2 | 12/2011 | Beals et al. |
| 8,088,163 B1 | 1/2012 | Kleiner |
| D655,414 S | 3/2012 | Cuschieri et al. |
| D656,610 S | 3/2012 | Kleiner |
| 8,148,326 B2 | 4/2012 | Beals et al. |
| D660,428 S | 5/2012 | Hohl |
| 8,198,238 B2 | 6/2012 | Beals et al. |
| 8,246,572 B2 | 8/2012 | Cantor et al. |
| 8,293,232 B2 | 10/2012 | Beals et al. |
| 8,361,152 B2 | 1/2013 | McCormack et al. |
| D692,133 S | 10/2013 | Steinwachs et al. |
| 8,834,472 B2 | 9/2014 | McCormack et al. |
| 8,932,295 B1 | 1/2015 | Greenhalgh |
| 8,945,137 B1 | 2/2015 | Greenhalgh et al. |
| 2002/0010472 A1 | 1/2002 | Kuslich et al. |
| 2002/0049448 A1 | 4/2002 | Sand et al. |
| 2002/0058947 A1 | 5/2002 | Hochschuler et al. |
| 2002/0099377 A1 | 7/2002 | Zucherman et al. |
| 2002/0116006 A1 | 8/2002 | Cohen |
| 2003/0083748 A1 | 5/2003 | Lee et al. |
| 2003/0149482 A1 | 8/2003 | Michelson |
| 2003/0171812 A1 | 9/2003 | Grunberg et al. |
| 2003/0229358 A1 | 12/2003 | Errico et al. |
| 2004/0002713 A1 | 1/2004 | Olson et al. |
| 2004/0024466 A1 | 2/2004 | Heerklotz et al. |
| 2004/0073314 A1 | 4/2004 | White et al. |
| 2004/0087956 A1 | 5/2004 | Weikel et al. |
| 2004/0133211 A1 | 7/2004 | Raskin et al. |
| 2004/0133217 A1 | 7/2004 | Watschke |
| 2004/0143330 A1 | 7/2004 | Sazy |
| 2004/0148027 A1 | 7/2004 | Errico et al. |
| 2004/0153158 A1 | 8/2004 | Errico et al. |
| 2004/0167532 A1* | 8/2004 | Olson et al. .......... 606/93 |
| 2004/0176853 A1 | 9/2004 | Sennett et al. |
| 2004/0215201 A1 | 10/2004 | Lieberman |
| 2004/0230211 A1 | 11/2004 | Moutafis et al. |

(56) References Cited

U.S. PATENT DOCUMENTS

| | | |
|---|---|---|
| 2005/0070900 A1 | 3/2005 | Serhan et al. |
| 2005/0096601 A1* | 5/2005 | Doyle .......................... 604/198 |
| 2005/0112091 A1 | 5/2005 | DiMauro et al. |
| 2005/0124993 A1 | 6/2005 | Chappuis |
| 2005/0124994 A1 | 6/2005 | Berger et al. |
| 2005/0149035 A1 | 7/2005 | Pimenta et al. |
| 2005/0149192 A1 | 7/2005 | Zucherman et al. |
| 2005/0159765 A1 | 7/2005 | Moutafis et al. |
| 2005/0165405 A1 | 7/2005 | Tsou |
| 2005/0216002 A1 | 9/2005 | Simonson |
| 2005/0216018 A1 | 9/2005 | Sennett |
| 2005/0251146 A1 | 11/2005 | Martz et al. |
| 2005/0251257 A1 | 11/2005 | Mitchell et al. |
| 2005/0261781 A1 | 11/2005 | Sennett et al. |
| 2005/0283150 A1 | 12/2005 | Moutafis et al. |
| 2006/0004367 A1 | 1/2006 | Alamin et al. |
| 2006/0015184 A1 | 1/2006 | Winterbottom et al. |
| 2006/0058585 A1 | 3/2006 | Oberlaender et al. |
| 2006/0058807 A1 | 3/2006 | Landry et al. |
| 2006/0100304 A1 | 5/2006 | Vresilovic et al. |
| 2006/0111779 A1 | 5/2006 | Petersen |
| 2006/0111780 A1 | 5/2006 | Petersen |
| 2006/0116770 A1 | 6/2006 | White et al. |
| 2006/0122597 A1 | 6/2006 | Jones et al. |
| 2006/0154366 A1 | 7/2006 | Brown et al. |
| 2006/0155170 A1 | 7/2006 | Hanson et al. |
| 2006/0167461 A1 | 7/2006 | Hawkins et al. |
| 2006/0190081 A1 | 8/2006 | Kraus |
| 2006/0229550 A1 | 10/2006 | Staid et al. |
| 2006/0247650 A1 | 11/2006 | Yerby et al. |
| 2006/0247791 A1 | 11/2006 | McKay et al. |
| 2006/0264808 A1 | 11/2006 | Staid et al. |
| 2006/0264964 A1 | 11/2006 | Scifert et al. |
| 2007/0003598 A1 | 1/2007 | Trieu |
| 2007/0043376 A1* | 2/2007 | Leatherbury et al. .......... 606/99 |
| 2007/0043442 A1 | 2/2007 | Abernathie |
| 2007/0067034 A1 | 3/2007 | Chirico et al. |
| 2007/0073110 A1 | 3/2007 | Larson et al. |
| 2007/0073294 A1 | 3/2007 | Chin et al. |
| 2007/0088007 A1 | 4/2007 | Ng |
| 2007/0093850 A1 | 4/2007 | Harris et al. |
| 2007/0123985 A1 | 5/2007 | Errico et al. |
| 2007/0172790 A1 | 7/2007 | Doucette, Jr. et al. |
| 2007/0185496 A1* | 8/2007 | Beckman et al. ............... 606/93 |
| 2007/0208423 A1 | 9/2007 | Messerli et al. |
| 2007/0213596 A1 | 9/2007 | Hamada |
| 2007/0213717 A1 | 9/2007 | Trieu |
| 2007/0213718 A1 | 9/2007 | Trieu |
| 2007/0213822 A1 | 9/2007 | Trieu |
| 2007/0213826 A1 | 9/2007 | Smith et al. |
| 2007/0225219 A1 | 9/2007 | Boden et al. |
| 2007/0225811 A1 | 9/2007 | Scifert et al. |
| 2007/0242869 A1 | 10/2007 | Luo et al. |
| 2007/0250166 A1 | 10/2007 | McKay |
| 2007/0264300 A1 | 11/2007 | Scifert et al. |
| 2007/0265632 A1 | 11/2007 | Scifert et al. |
| 2007/0270951 A1 | 11/2007 | Davis et al. |
| 2007/0276406 A1 | 11/2007 | Mahoney et al. |
| 2007/0288007 A1 | 12/2007 | Burkus et al. |
| 2007/0293948 A1 | 12/2007 | Bagga et al. |
| 2008/0003255 A1 | 1/2008 | Kerr et al. |
| 2008/0009929 A1 | 1/2008 | Harris et al. |
| 2008/0033440 A1 | 2/2008 | Moskowitz et al. |
| 2008/0058606 A1 | 3/2008 | Miles et al. |
| 2008/0071284 A1* | 3/2008 | Lechmann et al. ............. 606/99 |
| 2008/0086142 A1 | 4/2008 | Kohm et al. |
| 2008/0125856 A1 | 5/2008 | Perez-Cruet et al. |
| 2008/0147191 A1 | 6/2008 | Lopez et al. |
| 2008/0154375 A1 | 6/2008 | Serhan et al. |
| 2008/0154377 A1 | 6/2008 | Voellmicke |
| 2008/0154381 A1 | 6/2008 | Parrish |
| 2008/0172127 A1 | 7/2008 | Perez-Cruet et al. |
| 2008/0195058 A1 | 8/2008 | Moutafis et al. |
| 2008/0228225 A1 | 9/2008 | Trautwein et al. |
| 2008/0243126 A1 | 10/2008 | Gutierrez et al. |
| 2008/0249569 A1 | 10/2008 | Waugh et al. |
| 2008/0255564 A1 | 10/2008 | Michelson |
| 2008/0255666 A1 | 10/2008 | Fisher et al. |
| 2008/0260598 A1 | 10/2008 | Scifert et al. |
| 2008/0269904 A1 | 10/2008 | Voorhies |
| 2008/0288071 A1 | 11/2008 | Biyani et al. |
| 2008/0300598 A1 | 12/2008 | Barreiro et al. |
| 2009/0043312 A1 | 2/2009 | Koulisis et al. |
| 2009/0076440 A1 | 3/2009 | Moutafis et al. |
| 2009/0076556 A1 | 3/2009 | McGarity et al. |
| 2009/0088765 A1 | 4/2009 | Butler et al. |
| 2009/0098184 A1 | 4/2009 | Govil et al. |
| 2009/0099660 A1 | 4/2009 | Scifert et al. |
| 2009/0105718 A1* | 4/2009 | Zhang et al. .................. 606/104 |
| 2009/0124860 A1 | 5/2009 | Miles et al. |
| 2009/0124980 A1 | 5/2009 | Chen |
| 2009/0125066 A1 | 5/2009 | Krau et al. |
| 2009/0142385 A1 | 6/2009 | Gross et al. |
| 2009/0187194 A1 | 7/2009 | Hamada |
| 2009/0192350 A1 | 7/2009 | Meja |
| 2009/0192403 A1 | 7/2009 | Gharib et al. |
| 2009/0198245 A1 | 8/2009 | Phan |
| 2009/0198249 A1 | 8/2009 | Ziegler |
| 2009/0198337 A1 | 8/2009 | Phan |
| 2009/0198338 A1 | 8/2009 | Phan |
| 2009/0198339 A1 | 8/2009 | Kleiner et al. |
| 2009/0203967 A1 | 8/2009 | Branch et al. |
| 2009/0204148 A1 | 8/2009 | Lenke |
| 2009/0204159 A1 | 8/2009 | Justis et al. |
| 2009/0204220 A1 | 8/2009 | Trieu |
| 2009/0222011 A1 | 9/2009 | Lehuec et al. |
| 2009/0228107 A1 | 9/2009 | Michelson |
| 2009/0246244 A1 | 10/2009 | McKay et al. |
| 2009/0248163 A1 | 10/2009 | King et al. |
| 2009/0259108 A1 | 10/2009 | Miles et al. |
| 2009/0264892 A1 | 10/2009 | Beyar et al. |
| 2009/0275995 A1 | 11/2009 | Truckai |
| 2009/0299477 A1 | 12/2009 | Clayton et al. |
| 2009/0306671 A1 | 12/2009 | McCormack et al. |
| 2009/0306692 A1 | 12/2009 | Barrington et al. |
| 2010/0004752 A1 | 1/2010 | White et al. |
| 2010/0010367 A1 | 1/2010 | Foley et al. |
| 2010/0010524 A1 | 1/2010 | Barrington et al. |
| 2010/0016903 A1 | 1/2010 | Matityahu et al. |
| 2010/0016972 A1 | 1/2010 | Jansen et al. |
| 2010/0016973 A1 | 1/2010 | de Villiers et al. |
| 2010/0021518 A1 | 1/2010 | Scifert et al. |
| 2010/0030065 A1 | 2/2010 | Farr et al. |
| 2010/0036226 A9 | 2/2010 | Marino et al. |
| 2010/0036442 A1 | 2/2010 | Lauryssen et al. |
| 2010/0042221 A1 | 2/2010 | Boyd |
| 2010/0057208 A1 | 3/2010 | Dryer |
| 2010/0063516 A1 | 3/2010 | Parmer et al. |
| 2010/0063554 A1 | 3/2010 | Branch et al. |
| 2010/0076335 A1 | 3/2010 | Gharib et al. |
| 2010/0076445 A1 | 3/2010 | Pagano |
| 2010/0076446 A1 | 3/2010 | Gorek |
| 2010/0082036 A1 | 4/2010 | Reiley et al. |
| 2010/0087828 A1 | 4/2010 | Krueger et al. |
| 2010/0087875 A1 | 4/2010 | McGahan et al. |
| 2010/0100141 A1 | 4/2010 | de Villiers et al. |
| 2010/0105986 A1 | 4/2010 | Miles et al. |
| 2010/0105987 A1 | 4/2010 | Miles et al. |
| 2010/0112029 A1 | 5/2010 | Scifert |
| 2010/0121365 A1 | 5/2010 | O'Sullivan et al. |
| 2010/0121453 A1 | 5/2010 | Peterman |
| 2010/0125333 A1 | 5/2010 | Zdeblick et al. |
| 2010/0125338 A1 | 5/2010 | Fitz |
| 2010/0131020 A1 | 5/2010 | Heinz et al. |
| 2010/0137690 A1 | 6/2010 | Miles et al. |
| 2010/0137923 A1 | 6/2010 | Greenhalgh et al. |
| 2010/0145390 A1 | 6/2010 | McCarthy et al. |
| 2010/0145391 A1 | 6/2010 | Kleiner |
| 2010/0145452 A1 | 6/2010 | Blaylock et al. |
| 2010/0145461 A1 | 6/2010 | Landry et al. |
| 2010/0160923 A1 | 6/2010 | Sand et al. |
| 2010/0160982 A1 | 6/2010 | Justis et al. |
| 2010/0161062 A1 | 6/2010 | Foley et al. |
| 2010/0161074 A1 | 6/2010 | McKay |

(56) References Cited

U.S. PATENT DOCUMENTS

| | | | |
|---|---|---|---|
| 2010/0168755 A1 | 7/2010 | Reiley et al. |
| 2010/0168862 A1 | 7/2010 | Edie et al. |
| 2010/0174326 A1 | 7/2010 | Selover et al. |
| 2010/0185286 A1 | 7/2010 | Allard |
| 2010/0185287 A1 | 7/2010 | Allard |
| 2010/0185288 A1 | 7/2010 | Carls |
| 2010/0191241 A1 | 7/2010 | McCormack et al. |
| 2010/0191334 A1 | 7/2010 | Keller |
| 2010/0191337 A1 | 7/2010 | Zamani et al. |
| 2010/0198140 A1 | 8/2010 | Lawson |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0249934 A1 | 9/2010 | Melkent |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0266689 A1 | 10/2010 | Simonton et al. |
| 2010/0280622 A1 | 11/2010 | McKinley |
| 2010/0286778 A1 | 11/2010 | Eisermann et al. |
| 2010/0286784 A1 | 11/2010 | Curran et al. |
| 2010/0298938 A1 | 11/2010 | Humphreys et al. |
| 2010/0305575 A1 | 12/2010 | Wilkinson et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2010/0331847 A1 | 12/2010 | Wilkinson et al. |
| 2010/0331891 A1 | 12/2010 | Culbert et al. |
| 2011/0014587 A1 | 1/2011 | Spagnoli et al. |
| 2011/0015748 A1 | 1/2011 | Molz, IV |
| 2011/0020768 A1 | 1/2011 | Spagnoli et al. |
| 2011/0021427 A1 | 1/2011 | Amsden et al. |
| 2011/0028393 A1 | 2/2011 | Vickers et al. |
| 2011/0071527 A1 | 3/2011 | Nelson et al. |
| 2011/0071536 A1 | 3/2011 | Kleiner |
| 2011/0093005 A1 | 4/2011 | Strokosz et al. |
| 2011/0106162 A1 | 5/2011 | Ballard et al. |
| 2011/0144755 A1 | 6/2011 | Baynham et al. |
| 2011/0160777 A1 | 6/2011 | Spagnoli et al. |
| 2011/0184412 A1 | 7/2011 | Scifert et al. |
| 2011/0230970 A1 | 9/2011 | Lynn et al. |
| 2012/0022651 A1 | 1/2012 | Akyuz et al. |
| 2012/0035668 A1 | 2/2012 | Manninen et al. |
| 2012/0059477 A1 | 3/2012 | Kleiner |
| 2012/0065613 A1 | 3/2012 | Pepper et al. |
| 2012/0065687 A1 | 3/2012 | Ballard et al. |
| 2012/0078315 A1 | 3/2012 | Sweeney |
| 2012/0259335 A1 | 10/2012 | Scifert et al. |
| 2013/0073041 A1 | 3/2013 | Scifert et al. |
| 2013/0110169 A1 | 5/2013 | Hynes et al. |
| 2014/0100657 A1 | 4/2014 | McCormack et al. |

FOREIGN PATENT DOCUMENTS

| | | |
|---|---|---|
| WO | WO 02/17801 | 3/2002 |
| WO | WO 2005/037149 | 4/2005 |
| WO | WO 2005/071190 | 8/2005 |

OTHER PUBLICATIONS

U.S. Appl. No. 29/415,847, filed Mar. 14, 2012, Kleiner.

Ray, C., "Facet Joint Disorders and Back Pain," published on Spine-Health, Dec. 10, 2002, available at www.spine-health.com/conditions/arthritis/facet-joint-disorders-and-back-pain, 1 page.

Staehler, R., "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.

Staehler, R., "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.

Ullrich, P.F., "Anterior Cervical Spinal Fusion Surgery," published on Spine-Health, Oct. 7, 2005, available at www.spine-health.com/treatment/back-surgery/anterior-cervical-spinal-fusion-surgery, 2 pages.

Ullrich, P.F., "Cervical Spinal Instrumentation," published on Spine-Health, Oct. 7, 2005, available at www.spine-health.com/treatment/back-surgery/cervical-spinal-instrumentation, 2 pages.

Wascher, T.M., "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.

"BAK® /Proximity™ (BP®) Cage", Zimmer Website, as early as Oct. 23, 2007, available at http://www.zimmer.com/z/ctl/op/global/action/1/id/7930/template/MP/prcat/M6/prod/y, printed on Jun. 8, 2009, 1 page.

"Bak® Vista® Radiolucent Interbody Fusion System", Zimmer Website, as early as Oct. 25, 2005, available at http://www.zimmerindia.com/z/ctl/op/global/action/1/id/7809/template/MP/prcat/M6/prod/y, printed on Jun. 8, 2009, pp. 1-2.

"Facet Joint Syndrome," The Cleveland Clinic Foundation, copyright 1995-2008, printed Nov. 19, 2008, available at http://my.clevelandclinic.org/disorders/facet_joint_syndrome/hic_facet_joint_syndrome.aspx, 2 pages.

"Screws, Cages or Both", Spine Universe Website, as early as Aug. 18, 2002, available at http://www.spineuniverse.com/displayarticle.php/article1363.html, printed on Jun. 8, 2009, pp. 1-13.

"University of Maryland Spine Program: A Patient's Guide to Anterior Lumbar Interbody Fusion with Intervertebral Cages", University of Maryland Medical Center website, as early as 2003, available at http://www.umm.edu/spinecenter/education/anterior_lumbar_interbody_fusion_with_intervertebral_cages.htm, printed on Jun. 8, 2009, pp. 1-4.

"Vertebral column," from Wikipedia, the free encyclopedia, printed May 19, 2009, retrieved from http://en.wikipedia.org/wiki/Vertebral_column, 6 pages.

"Zygapophysial joint," from Wikipedia, the free encyclopedia, printed May 19, 2009, retrieved from http://en.wikipedia.org/wiki/Zygapophysial_joint, 2 pages.

International Search Report for International (PCT) Patent Application No. PCT/US11/52278, mailed Jan. 18, 2012 2 pages.

Written Opinion for International (PCT) Patent Application No. PCT/US11/52278, mailed Jan. 18, 2012 5 pages.

International Search Report for International (PCT) Patent Application No. PCT/US2009/033488, mailed. Mar. 25, 2009, 2 pages.

Written Opinion for International (PCT) Patent Application No. PCT/US2009/033488, mailed. Mar. 25, 2009, 9 pages.

U.S. Appl. No. 13/473,366, filed May 16, 2012, Kleiner.

Official Action for U.S. Appl. No. 12/886,452, mailed May 9, 2012 19 pages.

U.S. Appl. No. 29/427,387, filed Jul. 17, 2012, Kleiner.

U.S. Appl. No. 13/632,956, filed Oct. 1, 2012, Kleiner.

U.S. Appl. No. 29/433,403, filed Sep. 28, 2012, Kleiner.

U.S. Appl. No. 13/714,971, filed Dec. 14, 2012.

Official Action for U.S. Appl. No. 12/886,452, mailed Oct. 16, 2012 15 pages.

Official Action for Australian Patent Application No. 2011305680, dated Jan. 31, 2014, 3 pages.

Notice of Allowance for Japanese Patent Application No. 2013-25835, mailed Mar. 28, 2014, 2 pages (includes English translation).

International Preliminary Report on Patentability for International (PCT) Patent Application No. PCT/US11/52278, mailed Apr. 4, 2013 7 pages.

U.S. Appl. No. 29/453,829, filed May 3, 2013, Kleiner.

U.S. Appl. No. 13/947,255, filed Jul. 22, 2013, Kleiner.

Ehrenberg, "The 3-D Printing Revolution," Science News, Mar. 9, 2013, pp. 20-25.

Notice of Allowance for U.S. Appl. No. 13/947,255, mailed Oct. 17, 2013 16 pages.

(56) References Cited

OTHER PUBLICATIONS

Notice of Allowance for U.S. Appl. No. 14/088,148, mailed Feb. 3, 2014 11 pages.
U.S. Appl. No. 13/754,042, filed Jul. 30, 2013, Kleiner.
International Search Report and Written Opinion for International (PCT) Patent Application No. PCT/US2013/023992 mailed Apr. 26, 2013, 8 pages.
Notice of Acceptance for Australian Patent Application No. 2011305680, dated Aug. 27, 2014, 2 pages.
Official Action for Canadian Patent Application No. 2,811,018, dated Feb. 6, 2014, 2 pages.
Official Action for European Patent Application No. 11827323.4, dated Jul. 21, 2014, 3 pages.
International Preliminary Report on Patentability for International (PCT) Patent Application No. PCT/US2013/023992 mailed Aug. 14, 2014, 6 pages.
Official Action for Canadian Patent Application No. 153952, dated Apr. 15, 2014, 1 page.
Notice of Allowance for U.S. Appl. No. 12/886,452, mailed Jul. 15, 2014 7 pages.
Notice of Allowance for U.S. Appl. No. 29/453,829, mailed Oct. 8, 2014, 8 pages.
U.S. Appl. No. 14/263,963, filed Apr. 28, 2014, Kleiner et al.
U.S. Appl. No. 29/506,748, filed Oct. 20, 2014, Grimberg et al.
Extended European Search Report for European Patent Application No. 11827323.4, dated Oct. 17, 2014, 9 pages.
U.S. Appl. No. 14/214,031, filed Mar. 14, 2014, Greenhalgh.
Official Action for Canadian Patent Application No. 2,811,018, dated Dec. 8, 2014, 3 pages.

* cited by examiner

SECTION A-A

SECTION A-A

SECTION A-A

FUSION CAGE WITH COMBINED BIOLOGICAL DELIVERY SYSTEM

CROSS REFERENCE TO RELATED APPLICATIONS

This application is a continuation-in-part of U.S. patent application Ser. No. 12/886,452, filed Sep. 20, 2010, which claims the benefit of U.S. Provisional Application No. 61/243,664, filed on Sep. 18, 2009, and cross-references U.S. Provisional Application No. 61/439,712, filed Feb. 4, 2011 and PCT Application No. IA PCT/US11/52278, filed Sep. 20, 2011, the entire disclosures of which are hereby incorporated herein by reference in their entirety.

FIELD OF THE INVENTION

This disclosure relates to orthopedic surgery, and more specifically to an apparatus and method for near-simultaneous and integrated delivery of bone graft material during the placement of surgical cages or other medical implants in a patient's spine.

BACKGROUND OF THE INVENTION

According to the American Academy of Orthopedic Surgeons, about 250,000 spinal fusion surgeries are performed every year, mostly on adults between the ages of 45 to 64. Spinal fusion is a process by which two or more of the vertebrae that make up the spinal column are fused together with bone grafts and internal devices (such as rods) that heal into a single solid bone. Spinal fusion can eliminate unnatural motion between the vertebrae and, in turn, reduce pressure on nerve endings. In addition, spinal fusion can be used to treat, for example, injuries to spinal vertebrae caused by trauma; protrusion and degeneration of the cushioning disc between vertebrae (sometimes called slipped disc or herniated disc); abnormal curvatures (such as scoliosis or kyphosis); and weak or unstable spine caused by infections or tumors.

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). A posterior approach is one that accesses the surgical site from the patient's back, and an anterior approach is one that accesses the surgical site from the patient's front or chest. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, the entire disclosure of which is incorporated by reference in its entirety.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvest. Each of the manufacturers espouses their product as the most advantageous for healing. These products all have similar handling characteristics and the literature reveals that they have similar healing prospects. They come in a syringe and it is up to the surgeon to apply the selected material to the target site. The most common site for application is to the disk space after it has been prepared to a bleeding bed and ready to accept a cage and/or the grafting material. This represents a long and narrow channel even in open procedures. The surgeon is left to his own devices as to how to get the graft from its container to the active site. The devices which have been used have included a "caulking gun" construct and a variety of barrel shaft with a plunger design.

Bone graft typically includes crushed bone (cancellous and cortical), or a combination of these (and/or other natural materials), and may further comprise synthetic biocompatible materials. Bone graft of this type is intended to stimulate growth of healthy bone. As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices in both prepackaged or packaged by the surgeon embodiments. In addition, the method of delivery of bone graft to a particular location varies depending on the form of the bone graft utilized.

Autogenous bone (bone from the patient) or allograft bone (bone from another individual) are the most commonly used materials to induce bone formation. Generally, small pieces of bone are placed into the space between the vertebrae to be fused. Sometimes larger solid pieces of bone are used to provide immediate structural support. Autogenous bone is generally considered superior at promoting fusion. However, this procedure requires extra surgery to remove bone from another area of the patient's body such as the pelvis or fibula. Thus, it has been reported that about 30 percent of patients have significant pain and tenderness at the graft harvest site, which may be prolonged, and in some cases outlast the back pain the procedure intended to correct. Similarly, allograft bone and other bone graft substitutes, although eliminating the need for a second surgery, have drawbacks in that they have yet to be proven as cost effective and efficacious substitutes for autogenous bone fusion.

An alternative to autogenous or allograft bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. However, use of BMPs, although efficacious in promoting bone growth, can be prohibitively expensive.

Another alternative is the use of a genetically engineered version of a naturally occurring bone growth factor. This approach also has limitations. Specifically, surgeons have expressed concerns that genetically engineered BMPs can dramatically speed the growth of cancerous cells or cause non-cancerous cells to become more sinister. Another concern is unwanted bone creation. There is a chance that bone generated by genetically engineered BMPs could form over the delicate nerve endings in the spine or, worse, somewhere else in the body.

Regenerative medicine, which harnesses the ability of regenerative cells, e.g., stem cells (i.e., the unspecialized master cells of the body) to renew themselves indefinitely and develop into mature specialized cells, may be a means of circumventing the limitations of the prior-art techniques. Stem cells, i.e., both embryonic and adult stem cells, have been shown to possess the nascent capacity to become many, if not all, of the 200+ cell and tissue types of the body, including bone. Recently, adipose tissue has been shown to be a source of adult stem cells (See e.g. Zuk, Patricia Z. et al., "Multilineage Cells from Human Adipose Tissue: Implication for Cell-Based Therapies," Tissue Engineering, April 2001, 7:211-28; Zuk, Patricia A. et al., "Human Adipose Tissue Is A Source Of Multipotent Stem Cells," Molecular Biology of the Cell, 2002, 13:4279-4295). Adipose tissue (unlike marrow, skin, muscle, liver and brain) is comparably easy to harvest in relatively large amounts with low morbidity (See e.g. Commons, G. W., Halperin, B., and Chang, C. C. (2001) "Large-volume liposuction: a review of 631 consecutive cases over 12 years" Plast. Reconstr. Surg. 108, 1753-63; Katz, B. E., Bruck, M. C. and Coleman, W. P. 3 (2001b) "The benefits of powered liposuction versus traditional liposuction: a paired comparison analysis" Dermatol. Surg. 27, 863-7). Accordingly, given the limitations of the prior art spinal fusion techniques, there exists a need for a device that incorporates regenerative cells, e.g., stem cells that posses the ability to induce bone formation.

Many different methods and approaches have been attempted to induce bone formation or to promote spinal fusion. The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or the chalking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device, and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device.

As mentioned, the method of delivery of bone graft to a particular location varies depending on the form of the bone graft utilized. For example, in the case of slurry type bone graft, various dispensing devices have been developed having applicators designed to accommodate this type of bone graft. One such device is disclosed by U.S. Pat. No. 5,925,051 issued to Mikhail on Jul. 20, 1999 ("Mikhail"). Mikhail provides a caulking gun type dispenser for introducing bone graft in an enlarged bone (e.g. femoral) cavity. The device preferably includes a barrel pre-loaded with bone graft and a cannulated ejector positioned over a multi-section guide wire. This arrangement purports to accomplish both ejecting bone graft from the barrel and compacting the bone graft material while being guided on the guide wire. Mikhail, however, is designed solely for use with slurry-type bone graft, and does not accommodate bone graft in granule form, which often varies in size among granules and does not have the same "flow" or viscosity characteristics as slurry-type bone graft. Thus, the applicator of Mikhail is insufficient for introducing most bone graft to a surgical site in a patient.

U.S. Pat. No. 6,019,765 issued to Thornhill et al. on Feb. 1, 2000 ("Thornhill") also teaches a bone graft delivery device. The bone graft device applicator of Thornhill is used to apply bone graft to an artificial joint without having to remove a previously implanted prosthesis component. The applicator device includes a hollow tube with an actuation mechanism for discharging the bone graft from the device via a nozzle coupled to a distal end of the tube. The bone graft delivery device of Thornhill may include various components for loading the device with the bone graft, and may further include a plurality of nozzles each having a geometry suited for a particular application. Like Mikhail, the Thornhill delivery device is designed for use with bone slurry, and requires much custom instrumentation and different sized parts to achieve success in many bone graft delivery applications, which in turn increases the time to assemble and use the delivery device and may create further problems during the surgical operation.

U.S. Pat. No. 5,697,932 issued to Smith et al. on Dec. 16, 1997 ("Smith") discloses yet another bone graft delivery system and method. In Smith, a hollow tube of pre-loaded bone graft and a plunger are used to facilitate delivery of the bone graft to a bone graft receiving area. A positioning structure is provided on the plunger to maintain the plunger in a desirable position with respect to the hollow tube. Adjunct positioning means may also be provided to ensure that the plunger remains in the desirable position during the packing of bone graft into the bone graft receiving area. Like the devices of Thornhill and Mikhail, the device disclosed by Smith is clearly designed solely for slurry type bone graft, and does not provide an effective opening for receiving the desired amount of bone graft. Furthermore, the hollow tube shown by Smith is narrow and does not have a footing or other apparatus associated with the delivery device for preventing the device from penetrating, for example, the abdominal region of a patient, which may occur during tamping or packing of the bone graft. This in turn may cause serious injury to a patient if not controlled, and for these reasons the device of Smith is also insufficient for delivery of bone graft to a surgical site.

Traditional devices for inserting a fusion cage or other medical implants into a patient's spine or other surgical area are distinct and separate from traditional devices that deliver bone graft material to the surgical site. For example, once an implant has been positioned, then bone growth material is packed into the internal cavity of the fusion cage. Also, sometimes the process is reversed, i.e., the bone growth is inserted first, and then the implant. These bone growth inducing substances come into immediate contact with the bone from the vertebral bone structures which project into the internal cavity through the apertures. Two devices are thus traditionally used to insert bone graft material into a patient's spine and to position and insert a fusion cage. These devices thus necessitate a disc space preparation followed by introduction of the biologic materials necessary to induce fusion and, in a separate step, application of a structural interbody fusion cage.

The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid 1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal fusion cages may be placed in front of the spine, a procedure known as anterior lumbar interbody fusion, or ALIF, or placed in back of the spine. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back.

A typical procedure for inserting a common threaded and impacted fusion cage is as follows. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space. Lastly, bone graft material may be inserted into the surgical area using separate tools and devices.

U.S. Pat. No. 4,743,256 issued to Brantigan ("Brantigan") discloses a traditional spinal back surgical method involving the implantation of a spinal fusion cage. The cage surfaces are shaped to fit within prepared endplates of the vertebrae to integrate the implant with the vertebrae and to provide a permanent load-bearing strut for maintaining the disc space. Brantigan teaches that these cages typically consist of a homogeneous nonresorbable material such as carbon-reinforced polymers such as polyether ether ketone (PEEK) or polyether ketone ether ketone ketone ("PEKEKK"). Although these cages have demonstrated an ability to facilitate fusion, a sufficient fusion is sometimes not achieved between the bone chips housed within the cage and the vertebral endplates. In particular, achieving a complete fusion in the middle portion of the cage has been particularly problematic. As shown in FIG. 6 herein, the upper U and lower L surfaces of these cages C have large transverse pores P which facilitate bone ingrowth, and these pores lead to an inner void space IVS which houses bone graft (not shown) which facilitates the desired fusion. In any case, Brantigan teaches the separate process and procedure for the insertion of a fusion cage and the insertion of bone graft. Indeed, local bone graft harvested from the channel cuts into the vertebrae to receive the plug supplements the fusion.

U.S. Pat. Appl. 20070043442 of Abernathie et al. ("Abernathie") discloses another traditional spinal back surgical method involving the implantation of a spinal fusion cage. Abernathie relates generally to an implantable device for promoting the fusion of adjacent bony structures, and a method of using the same. More specifically, Abernathie relates to an expandable fusion cage that may be inserted into an intervertebral space, and a method of using the same. Abernathie includes an aperture in the fusion cage to allow bone growth therethrough, as a separate procedure to the insertion of the fusion cage.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

U.S. Pat. No. 5,906,616 issued to Pavlov et al. ("Pavlov") discloses a fusion cage of various cylindrical and conical shapes and a method of insertion. Like Brantigan, Pavlov teaches the separate process and procedure for the insertion of a fusion cage and the insertion of bone graft. U.S. Pat. No. 5,702,449 ("McKay") discloses a spinal implant comprising a cage made of a porous biocompatible material reinforced by an outer sleeve made of a second material which is relatively stronger under the compressive load of the spine than the biocompatible material. U.S. Pat. No. 6,569,201 issued to Moumene et al. ("Moumene") teaches a bone fusion device having a structural bioresorbable layer disposed upon the outer surface of a non-resorbable support. As the bioresorbable structural layer resorbs over time, the load upon the bone graft housed within the non-resorbable support increases. Published PCT Application No. WO 99/08627 ("Gresser") discloses a fully bioresorbable interbody fusion device, as well as homogeneous composite devices containing at least 25% resorbable materials. U.S. Pat. No. 7,867,277 issued to Tohmeh discloses a spinal fusion implant of bullet shaped end.

U.S. Pat. No. 7,846,210 issued to Perez-Cruet et al. ("Perez-Cruet") discloses an interbody device assembly consisting of a fusion device and an insertion device. The insertion device positions the fusion device between two vertebrae, provides bone graft material, and then detaches from the fusion device, leaving the fusion device in place to restore disc space height. However, the Perez-Cruet device is designed to receive bone graft material from its insertion device and distribute the material away from the fusion device. In most embodiments of the fusion device, a center plate is positioned immediately downstream of the received bone graft material and directs the bone graft to opposing sides of the fusion device. (See, for example, FIG. 20 depicting plate 308 directing bone graft material 392 along the exterior sides of the fusion device 302). As such, the Perez-Cruet fusion device is unlikely to completely fill the areas near of its fusion cage and deliver bone graft material to the surrounding bone graft site. Furthermore, none of the Perez-Cruet fusion device embodiments feature a defined interior space or a cage-style design. Indeed, the Perez-Cruet fusion device explicitly teaches away from a contained-interior, fusion-cage-style device, asserting that its fusion device fills all of the disc space as opposed to a cage design, which contains the bone material. Furthermore, the Perez-Cruet does not feature a distal tip that functions to precisely position the fusion device and stabilize the device during delivery of bone graft material.

U.S. Pat. No. 7,985,256 issued to Grotz et al. ("Grotz") discloses an expandable spinal implant for insertion between opposed vertebral end plates. The implant is a cylinder block of slave cylinders; a central cavity between the cylinders receives bone graft material and pistons positioned within the cylinders provide a corrective bone engaging surface for expanding against a first vertebral end plate. The insertion tool used to place the spinal implant includes a handle and hollow interior for housing hydraulic control lines and a bone graft supply line. The Grotz system does not allow precise positioning or delivery of bone graft material without an implant and requires a complex and bulky insertion tool.

U.S. Pat. Appl. 2010/0198140 to Lawson ("Lawson") discloses a tool comprising a cannula with an open slot at the distal end and a closed tip. Lawson's tool employs tamps to push bone aside and open up a void for filling; solid bone pellets are then rammed down the hollow interior of the cannula by a tamper and delivered to the surgical site. Lawson does not allow precise positioning or delivery of viscous bone graft material and has no capability to interconnect or integrate with an implant such as a bone graft fusion cage.

U.S. Pat. Appl. 2010/0262245 to Alfaro et al. ("Alfaro") discloses a delivery system for an intervertebral spacer and a bone grafting material comprising a spacer disengagingly attached to a hollow handle. The handle comprises a chamber and bone grafting material-advancing means for introducing bone grafting material from the chamber into the spacer and the intervertebral spaces. The Alfaro system does not allow precise positioning or delivery of bone graft material through a distal tip that precisely positions the fusion device and stabilizes the device during delivery of bone graft material, and does not allow primarily lateral injection of bone graft fusion material.

The prior art bone graft delivery devices listed above typically must come pre-loaded with bone graft, or alternatively require constant loading (where permissible) in order to constantly have the desired supply of bone graft available. Moreover, these bone graft delivery devices generally cannot handle particulate bone graft of varying or irregular particulate size. Furthermore, the prior art devices for inserting a fusion cage or other medical implant into a patient's spine or other surgical area are commonly distinct and separate from traditional devices that deliver bone graft material to the surgical site. As such, two devices are traditionally used to insert bone graft material into a patient's spine and to position and insert a fusion cage. The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures. These problems can be a great inconvenience, cause avoidable trauma to a patient and make these prior art devices unsuitable in many procedures.

Therefore, there is a long-felt need for an apparatus and method for near-simultaneous and integrated precision delivery of bone graft material during the placement of surgical cages or other medical implants in a patient's spine. The present invention solves these needs. The present invention allows biologic material to flow directly to the fusion cage and be dispersed within the disc space in a single step, and can precisely and simply deliver particulate bone graft of varying or irregular particulate size. Thus, the present invention allows application of bone graft material through a detachable fusion cage, eliminates otherwise restriction of the volume of biologic material that may be dispersed within the disk space, and eliminates the requirement that the fusion cage be pushed back into the same place that the fusion material delivery device was, which can lead to additional trauma to the delicate nerve structures.

SUMMARY OF THE INVENTION

Certain embodiments of the present disclosure relate to an apparatus and method for near-simultaneous and integrated delivery of bone graft material during the placement of surgical cages or other medical implants in a patient's spine. The integrated fusion cage and delivery device (the "device") is comprised generally of a tubular member and a plunger for expelling bone graft from the tubular member, through a surgical fusion cage, and into a bone graft receiving area, then disengaging the fusion cage at the surgical site in a human patient. Thus, the apparatus and method allows the biologic material to flow directly into and through the fusion cage and dispersed within the disc space in a single step, and leave the detachable fusion cage in the surgical area. Other embodiments and alternatives to this device are described in greater detail below.

By way of providing additional background, context, and to further satisfy the written description requirements of 35 U.S.C. §112, the following references are incorporated by reference in their entireties for the express purpose of explaining the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

By way of providing additional background, context, and to further satisfy the written description requirements of 35 U.S.C. §112, the following references are incorporated by reference in their entireties for the express purpose of explaining the nature of the surgical procedures in which fusion cages are used and to further describe the various tools and other apparatus commonly associated therewith: U.S. Pat. No. 6,569,201 to Moumene et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. 2011/0015748 to Molz et al.; U.S. Pat. Appl. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. 2010/0198140 to Lawson; and U.S. Pat. Appl. 2010/0262245 to Alfaro et al.

By way of providing additional background and context, the following references are also incorporated by reference in their entireties for the purpose of explaining the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov; and U.S. Pat. No. 8,088,163 to Kleiner.

According to varying embodiments described herein, the present invention is directed to near-simultaneous and integrated delivery of bone graft material during the placement of surgical cages or other medical implants into a patient's spine. The delivery of the bone graft material may be to any area of the body, and in particular to the intervetebral joints of the spine, for achieving bone graft fusion. The device may be used without the optional near-simultaneous and integrated placement of surgical cages with the delivery of bone graft material. Also, the invention may be used in the repair of a bone joint or in connection with the implantation of prosthetic devices in the body, including, by way of example but not limitation, the hip, knee and a variety of spinal joints. Additionally, the present invention may be used in primary surgery, in which a bone graft is being supplied to promote new bone growth or to reconstruct a joint for the first time, as well as in revision surgery, in which a follow-up procedure is being performed in an area that has previously been subject to one or more surgeries. Further, the invention may be used in any application where material is to be delivered with precision to a confined area where access is restricted, to include surgical procedures, repair of installed or uninstalled mechanical or electrical devices, and arming or disarming of explosive devices.

Although well suited for use in human patients, and although much of the discussion of the present invention is directed toward use in humans, advantages offered by the present invention may be realized in the veterinary and scientific fields for the benefit and study of all types of animals and biological systems. Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas, specifically where there is a desire to constrain added fluid material to particular regions. For example, the present invention finds application in methods where the objective is to confine added material to predetermined areas of interest and to prohibit the undesired translocation of such material until an operation is complete and/or until a predetermined later time.

According to various embodiments of the present disclosure, one aspect of the invention is to provide an integrated fusion cage and graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space. A substantially round shape may also be employed that provides the surgeon with an indication of directional orientation.

The phrase "removably attached" and/or "detachable" is used herein to indicate an attachment of any sort that is readily releasable.

The phrase "integrated fusion cage", "spinal fusion implant", "biological implant" and/or "fusion cage" is used here to indicate a biological implant.

According to various embodiments of the present disclosure, it is another aspect that the hollow tubular member further comprise at least one opening on a lateral face or surface of the hollow tubular member, at one distal end, for ejecting bone graft material into a bone graft receiving area, such as a disc space, such that the bone graft material is ejected from the hollow tubular member through an additional implant, such as a structural cage implant. In addition, the graft material is dispersed into the area of the debrided disc space surrounding and within the cage. Furthermore, the structural cage implant is removably attached to the hollow tubular member so as to be deposited into the surgical area. Thus, the device may be used in an integrated and near-simultaneous method for depositing bone graft material into a debrided disc space through a structural cage implant and leaving the structural implant.

According to various embodiments of the present disclosure, one aspect of the invention is to provide an integrated fusion cage detachable component of the integrated fusion cage and graft delivery device that comprises a biological implant that fits over the distal end of the substantial hollow tube, and which has a shape that is substantially congruent with the distal end of the hollow tube. However, the shape and configuration of the integrated fusion cage need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space. A substantially round shape may also be employed that provides the surgeon with an indication of directional orientation.

In a preferred embodiment, the fusion cage has a tapered tip, and several open channels along the medial surfaces. In a preferred embodiment, the fusion cage and/or the bone graft delivery portion of the integrated fusion cage and graft delivery device is of oblong or rectangular, or square shape. The integrated fusion cage and graft delivery device is designed to avoid blocking or impacting bone graft material into a surgical disc space, thereby limiting the bone graft material that may be delivered, and not allowing available fusion space to be fully exploited for fusion.

In a preferred embodiment, the fusion cage has a keel-shaped tip to separate disk and prevent annular penetration. Also, the fusion cage has dual portals for bone graft discharge, with the medial openings larger than the lateral openings. Further, the fusion cage may be designed in variable heights and lengths so that it fits snugly into the prepared disk space.

In another embodiment of the device, the hollow tube engages with the fusion cage via a break-off collar and the plunger inserts into the interior of the hollow tube. The break-off collar may be severed by any of several means, to include application of torsion and/or rotational force and/or lateral force to the break-off collar, for example by twisting on the hollow tube and/or the plunger. The break-off collar may be formed by any of several means, comprising a thinner and/or reduced cross-sectional, that is thickness, a pre-set fracture-line, one or more notches, and any means known to those skilled in the art to achieve reliable break-off. In one example method of use, the connected hollow tube and fusion cage is inserted into the surgical area, bone graft material is inserted into the hollow tube (or already provided as a pre-packaged material), the plunger is pushed into the hollow tube, so as to deliver bone graft material to the site, then the plunger is reversed or pulled-out so to retreat from the site and move higher or beyond the break-off collar, and then the break-off collar is broken so as to disengage the fusion cage from the hollow tube and therein leave the fusion cage at the surgical site.

In another embodiment of the device, the hollow tube engages with a connector conduit which in turn connects with the fusion cage via a break-off collar. One or more connectors connect the hollow tube with the connector conduit. The hollow tube fits over the connector conduit. The one or more connectors fit through the hollow tube and the connector conduit. Alternately, the hollow tube may fit over the connector conduit via a press-fit, aka interference fit, without need of one or more connectors. In one embodiment, the connectors comprise set screws, pins and tabs. The connector conduit allows, for example, various fusion cages designs to be fitted to a common hollow tube/plunger combination. This allows, for example, the common hollow tube/plunger combination to be re-sterilized and thus reused in multiple surgical procedures. In one embodiment, the hollow tube/plunger combination is re-usable and the fusion cage is disposable.

In one embodiment of the connector conduit, the connector conduit is of circular cross-section. In another embodiment, the connector conduit is of conical shape, or any shape that allows a transition in diameter between the fusion cage and the follow tube.

In one example method of use, the hollow tube is inserted over the connection conduit (which is attached to the fusion cage), then inserted into the surgical area, bone graft material is inserted into the hollow tube (or already provided as a pre-packaged material), the plunger is pushed into the hollow tube (and past the connection conduit), so as to deliver bone graft material to the site, then the plunger is reversed or pulled-out so to retreat from the site and move higher or beyond the break-off collar, and then the break-off collar is broken so as to disengage the fusion cage from the hollow tube (which is still connected to the connection conduit) and therein leave the fusion cage at the surgical site.

The break-off collar may be severed by any of several means, to include application of torsion and/or rotational force and/or lateral force to break-off collar, for example by twisting on the hollow tube and/or the plunger.

In one embodiment of the fusion cage, the fusion cage is of rectangular cross-section, such that one pair of opposite sides, for example a height first pair of sides, has a dimension of approximately 8-14 mm, and a second pair of opposite sides, for example a length dimension, of approximately 22-36 mm. One skilled in the art will appreciate that the exact dimensions of the fusion cage may be adapted to conform to particulars of the surgical site, for example, the relative sizing between the particular vertebrae in which bone graft material and/or a fusion cage is to be inserted.

A preferred method of using the integrated fusion cage and graft delivery device comprises precisely inserting the integrated fusion cage and graft delivery device, in one or more of the embodiments contained herein, into the surgical area. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area through and into the surgical implant cage. The surgical implant device may then be selectably detached from the integrated fusion cage and graft delivery device so as to remain at the surgical site.

Another method of using the integrated fusion cage and graft delivery device comprises inserting the integrated fusion cage and graft delivery device into a prepared disk space, such that the fusion cage portion fits snugly into the prepared disk space (the fusion cage is designed in variable heights and lengths so as to fit snugly into the prepared disk space), pushing the plunger through the hollow shaft so as to push biological fusion material (e.g. bone graft) through the hollow shaft to flow the biological material through the fusion cage's open lateral and/or medial portals in communication with the hollow tube and plunger, thereby delivering biological material into the prepared disk space, after which the fusion cage is detached from the hollow tube and left in the disk space. Thus, the fusion cage is left in the disk space with a maximum and/or optimal amount of biological material near-simultaneously delivered within the fusion cage and/or surrounding the fusion cage in the disk space.

Using the integrated fusion cage and graft delivery device as described overcomes a problem associated with the traditional separate application of bone graft material and insertion of a fusion cage. Specifically, in the traditional method, the volume of disk space which does not contain bone graft material is limited, which, for example, limits the effectiveness of the surgical procedure. For example, using the traditional two-step procedure, bone graft may be inserted into, for example, a cylindrically-shaped area of radius r to a height h of 8 mm, and then a cylindrically-shaped fusion cage inserted of height h of 14 mm. Thus, the surgical area is left without a complete volume of bone graft material, i.e. because the volume of a cylinder is Volume=$\pi r^2$ h, the bone graft area is left without $\pi r^2$(14 mm-8 mm), or $6\pi r^2$ of bone graft material. (Note that this represents a 75% increase in bone graft material delivered to the surgical site for these example dimensions). This effectively dilutes the bone graft material and reduces its effectiveness. The present invention can substantially or completely fill the available disk space with bone graft material, because distraction of the disk space is performed substantially simultaneously with application of the fusion cage. Because more biological material is delivered to the prepared disk space, the fusion rate should increase. Also, by directly implanting fusion material, e.g. bone graft material, though a fusion cage positioned for detachment (and then detached) as a single step, time is saved and there is less manipulation of the sensitive nerve tissue at the fusion site (which increases safety).

Furthermore, the integrated fusion cage and graft delivery device may be used without the surgical implant delivery device portion such that the method comprises precisely inserting the integrated fusion cage and graft delivery device, in one or more of the embodiments contained herein, into the surgical area that may already contain one or more additional implants, such as a structural cage implant. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area without depositing bone graft material into the path of any structural cage implant or other implant that may already be present.

According to a still further aspect of the present invention, the integrated fusion cage may be introduced into a spinal target site without the use of the graft delivery device that is through use of any of a variety of suitable surgical instruments having the capability to engage the implant. The integrated fusion cage is capable of being used in minimally invasive surgical procedures, needing only a relatively small operative corridor for insertion.

According to a still further aspect of the present invention, the integrated fusion cage of the present invention may be used in a variety of configurations in a fusion procedure, including but not limited to (and by way of example only) unilateral, paired unilateral and bilateral.

Furthermore, the integrated fusion cage and graft delivery device and method of use is applicable to position and deliver fusion cages from the side, directly anterior or in the anterior fusion cages of the cervical spine.

In a preferred embodiment, the integrated fusion cage and graft delivery device comprises a hollow tube or contains at least one inner lumen constructed to receive bone graft, and a plunger adapted for insertion at least partially within the hollow tube and preferably through the full extent of the hollow tube. The plunger of some embodiments is generally of the same geometric configuration as the hollow interior potion of the hollow tube so that the plunger, once fully inserted in to the hollow tube, is substantially congruent with the hollow interior portion of the hollow tube, e.g. both the plunger and the hollow tube are substantially the same shape and/or class. The plunger preferably extends about the same length as the hollow tube, and further comprises an end portion, e.g. at least one knob or handle for grasping and manipulation by a user, or in robotic or automated or semi-automated control or surgeries, by a machine.

Also according to a preferred embodiment, the hollow interior portion of the hollow tube further comprises a sloped or curved surface at a second end (e.g. positioned near a place for deposit of bone graft material) adjacent and opposite a lateral window or opening in a lateral face of the hollow tube. As the interior of the hollow tube comprises a sloped or curved surface at its second end, the plunger also comprises a sloped or curved surface at a second end of the plunger. The plunger terminates opposite the curved surface at its second end with a laterally faced surface, which corresponds to the lateral window or opening at the second end of the hollow tube. The distal end of the hollow tube is fitted with a substantially conformal fusion cage that covers the exterior surface of the hollow tube, fitted with one or more openings that align with one or more openings of the hollow tube. Thus, in cooperation, the plunger may be inserted into the opening of the hollow tube, and extended the entire length of the hollow tube, at least to a point where the laterally faced surface of plunger is in communication with the lateral window or opening at the second end of the hollow tube. This configuration permits a user to eject substantially all of the bone graft material that is placed into the hollow tube in a lateral direction at the bone graft receiving area, through the substantially conformal and detachable fusion cage that covers the exterior surface of the hollow tube, optionally detach the detachable fusion cage, during a surgical procedure.

In a preferred embodiment, the integrated fusion cage and graft delivery device comprises an integrated fusion cage that comprises a first proximal end and a second distal end, wherein the first proximal end contains an opening adapted to allow fitting and/or engagement to the distal end of the hollow tube. This fitting and/or engagement may be over the external surface of the hollow tube or inside the interior of the hollow tube. Further, the integrated fusion cage may comprise one or more medial openings and one or more lateral openings that align with one or more openings at the distal end of the hollow tube. Further, the integrated fusion cage may contain surfaces, such as belts or striations, along one or more medial surfaces of the integrated fusion cage. The integrated fusion cage is configured such that when a plunger, once fully inserted in to the hollow tube, is substantially congruent with the hollow interior portion of the hollow tube, e.g. both the plunger and the hollow tube are substantially the same shape and/or class and bone graft material is delivered through the integrated fusion cage into the surgical area.

The spinal fusion implant of the present invention may be used to provide temporary or permanent fixation along an orthopedic target site.

The spinal fusion implant of the present invention may be provided with any number of additional features for promoting fusion, such as one or more apertures extending between the top and bottom surfaces which allow a boney bridge to form through the spinal fusion implant.

The spinal fusion implant may also be provided with any number of suitable anti-migration features to prevent the implant from migrating or moving from the disc space after implantation. Suitable anti-migration features may include, but are not necessarily limited to, angled teeth or ridges formed along the top and bottom surfaces of the implant and/or rod elements disposed within the distal and/or proximal ends.

According to a further aspect of the present invention, the spinal fusion implant may be provided with one or more radiographic markers at the proximal and/or distal ends. These markers allow for a more detailed visualization of the implant after insertion (through radiography) and allow for a more accurate and effective placement of the implant.

According to a still further aspect of the present invention, the distal end of the spinal fusion implant may have a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

Another embodiment for the integrated fusion cage and graft delivery device comprises a detachable fusion cage that is detachable, or removably attached, by any of several means. As disclosed above, in one embodiment, the fusion cage is substantially conformal with the distal end of the hollow tube in that it covers the exterior surface of the hollow tube, wherein the fusion cage is configured with one or more openings that align with one or more openings of the hollow tube. In one preferred embodiment, the fusion cage of the integrated fusion cage and graft delivery device forms an interference fit with the fusion cage, such that when the integrated fusion cage and graft delivery device is inserted into the surgical area, the integrated fusion cage and graft delivery device presses against bone and/or vertebrates such that when an axial force is applied to the integrated fusion cage and graft delivery device in a rearward direction (toward the proximal end of the integrated fusion cage and graft delivery device), the fusion cage detaches from the integrated fusion cage and graft delivery device and thereby remains in the surgical area.

In another embodiment for the integrated fusion cage and graft delivery device and its method of use, the fusion cage is substantially filled with bone graft material after the fusion cage is implanted. In another embodiment for the integrated fusion cage and graft delivery device and its method of use, the fusion cage is substantially filled with bone graft material simultaneously with the implantation of the fusion cage.

In another embodiment for the integrated fusion cage and graft delivery device and its method of use, the fusion cage and/or the bone graft material associated with the fusion cage may be accessed during subsequent surgical operations.

In another embodiment for the integrated fusion cage and graft delivery device and its method of use, the fusion cage is a separate device, for example a pre-packaged implant device, which may be installed independently from the integrated fusion cage and graft delivery device or installed in coordination with the integrated fusion cage and graft delivery device. In either situation, the device may be used to provide bone graft material in and/or around the pre-packaged implant.

In another embodiment for the integrated fusion cage and graft delivery device and its method of use, some or all of the bone graft material is provided as a component of a per-packaged implant. In another embodiment for the integrated fusion cage and graft delivery device, the detachable fusion cage is detachable by way of a indent-tab that penetrates the interior of the hollow tube, such, when the plunger is substantially inserted into the hollow tube, the indent-tab is pushed out from the interior of the hollow tube so as to no longer be attached to the integrated fusion cage and graft delivery device, thereby remaining in the surgical area.

In another embodiment, the hollow tube is of cylindrical shape and includes one or more locking tabs or indent tabs configured to engage one or more locking slots of the fusion cage. The locking tabs may permanently or not permanently engage the locking slots, and may be of a shape to include rectangular, circular and oblong. In one embodiment of the locking tabs and locking slots, the locking tabs and locking slots engage one another by rotating the hollow tube clockwise and are released by counterclockwise rotation. In another embodiment of the configuration of the locking tabs and locking slots, the locking tabs and locking slots engage one another by rotating the hollow tube counterclockwise and are released by clockwise rotation.

In another embodiment, the fusion cage has internal ramps which assist in directing the bone graft material to one or more openings in the fusion cage.

In another embodiment for the integrated fusion cage and graft delivery device, the detachable fusion cage is detachable by way of receipt of an electrical, mechanical, pneumatic, hydraulic or other communication imparted by the user upon the plunger and/or hollow tube so as to detach the fusion cage and thereby deposit the fusion cage into the surgical area.

In another embodiment for the integrated fusion cage and graft delivery device, the detachable fusion cage is detachable by way of a Luer taper or Luer fitting connection, such as in a Luer-Lok® or Luer-Slip® configuration or any other Luer taper or Luer fitting connection configuration. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0124980 to Chen.

In another embodiment for the integrated fusion cage and graft delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0187194 to Hamada.

In another embodiment for the integrated fusion cage and graft delivery device, the detachable fusion cage is detachable by use of magnetism. More specifically, the detachable fusion cage can be made to feature a magnetic field pattern and a resulting force R that are adjustable and may be of different character than the rest of the integrated fusion cage and graft delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the integrated fusion cage and graft delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the integrated fusion cage and graft delivery device can be arranged to present one or more openings between members or portions, where such openings extend between end portions of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2011/0015748 to Molz et al.

In another embodiment for the integrated fusion cage and graft delivery device, the detachable fusion cage is detachable by use of plasma treatment. The term "plasma" in this context is an ionized gas containing excited species such as ions, radicals, electrons and photons. (Lunk and Schmid, Contrib. *Plasma Phys.*, 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 *Polymeric Materials Encyclopedia* 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the integrated fusion cage and graft delivery device, or to provide selectable detachment of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Pat. No. 7,749,555 to Zanella et al.

One having skill in the art will appreciate that the fusion cage may be selectably detachable to the integrated fusion cage and graft delivery device, for example, by means that mechanically grasp the head, means that attach by vacuum, and means that attach by friction, or other means known to those of skill in the art for attaching the head of an apparatus to the shaft of an apparatus.

It is another aspect of the present disclosure that the distal end of the integrated fusion cage and graft delivery device be equipped with various other tools to aid in the procedure. Such tools may include, for example, devices used to assess the condition of the implantation site and surrounding tissue. This may include, for example, a device that transmits or provides an image or signal which carries an image for visual inspection and photography. Such an image capture device may include, for example, a device to illuminate the implant site coupled with an image capture and/or transmission device. Another tool may also include, for example, a device that aids in irrigation or drainage of the surgical site, a tool used to sample or biopsy tissue.

Another embodiment for the integrated fusion cage and graft delivery device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into said hollow tube, whereby the plunger has a distal end that is contoured to an interior surface of the distal end of the hollow tube such that the contoured distal end of the plunger is nearly congruent with the interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunder along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360 degree rotation of the plunger equates to 5 cc of bone graft material delivered to the bone graft site.

Another aspect of the present invention includes providing a hollow tube and plunger assembly, in which the hollow tube and/or the plunger assembly are disposable. The tube may also be at least portions of biocompatible material which can stay in the canal without impairing the final implantation. Alternatively, it may thus be a material that is resorbable, such as a resorbable polymer, in the canal after implantation, so as not to interfere with the growth of the bone or stability of the implant.

A further embodiment of the invention provides pre-packaged inserts for loading into the hollow tube element, or if there are a plurality of hollow tube elements, into one or more of the hollow tube elements. The pre-packaged inserts may be of varying lengths, and/or layered of differing materials or components, to include the patient's own bone graft matter.

Another embodiment of the present invention provides an integrated fusion cage and graft delivery system, by which a hollow tube and/or a hollow tube/plunger assembly can be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

A further embodiment of the present invention provides a bone graft insertion apparatus comprising a hollow tube constructed to receive bone graft, the hollow tube having a proximal and distal end whereby the hollow tube contains least one opening on a surface of the distal end of the hollow tube. The at least one opening is preferably positioned other than completely along the axial or longitudinal axis of the device. The number and size and shape of such openings can vary but are preferably adapted to deliver bone graft material in a direction substantially transverse to the axial extent of the substantially hollow tube. In one embodiment, two or more apertures are provided. In certain embodiments, apertures are on the same side of the hollow tube, where in others, apertures are on different sides (e.g. opposing sides) of a hollow tube. A plunger, adapted for insertion at least partially within the hollow tube, is constructed and arranged with respect to the hollow tube so as to present at least one substantially flat contour, whereby the plunger has a distal end that is contoured to an interior surface of the distal end of the hollow tube such that the contoured distal end of the plunger is nearly congruent with the interior surface of the distal end of the hollow tube. This facilitates removing substantially all of the bone graft received by the hollow tube whereby the bone graft is delivered to the graft receiving area. It is important to remove substantially all of the bone graft material as it is expensive and/or difficult to obtain.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such asguidewires along the longitudinal axis of the shaft of the plunger.

In another embodiment of the invention, the distal end and the proximal end of the hollow tube are in communication via a conduit to enable electrical, hydraulic, pneumatic, or mechanical transmission, the later such as a wire. Such hydraulic communication allows, for example, a medical or other liquid to be delivered or extracted from the surgical area. Such mechanical communication allows, for example, the distal end to be maneuvered precisely.

In another embodiment of the present disclosure, the hollow tube and/or plunger may be curved and/or may have an angular aspect, in addition to the sloped or curved surface at a second end of the hollow tube/plunger. This shape may, for example, aid the surgeon in more comfortably introducing the delivery device to the implant site, be shaped to better accommodate implantation sites on right or left sides of the body, or be shaped to better accommodate right or left-handed surgeons. One having skill in the art will appreciate that the delivery device may have multiple angles and curved aspects which enable aspects of embodiments of the present disclosure or aid in ergonomics.

In one embodiment of the present disclosure, the device further comprises a footing or shelf at the distal end of the tubular device that is nearest the operating site for preventing or mitigating risk of injury to the patient during surgery. According to this embodiment, the footing may be flexible, semi-flexible, semi-rigid or rigid. The footing serves to protect the anatomy of the patient from being penetrated by the hollow tube of the integrated fusion cage and graft delivery device when the plunger is being inserted or during tamping of the hollow tube or the plunger by the surgeon, which may occur during the surgical procedure for a variety of reasons. In certain embodiments, the distal tip region of the hollow tube comprises a softer, maliable and/or less rigid material than the remainder of the hollow tube. For example, the distal tip could be made of a bioactive collagen.

It is yet another aspect of the present disclosure to provide a integrated fusion cage and graft delivery device that contains one or more detachable elements for use in an operation where bone graft material must be inserted into the integrated fusion cage and graft delivery device and ejected to a bone graft receiving area. According to various embodiments, these detachable devices may include a detachable funnel for gathering and inserting bone graft material at a graspable end of the integrated fusion cage and graft delivery device. The present disclosure may also comprise a plunger that has a detachable handle, which may be selectively removed to avoid blocking the surgeon's view of the operating site. The integrated fusion cage and graft delivery device may further comprise a detachable footing or shelf at one distal end of the hollow tubular member. In one embodiment this footing or shelf is selectively positionable about various points along the hollow tube. For example, a distal portion of the hollow tube has a rotatable portion that can be positioned to deliver bone graft material to areas of a disc space in a manner such that a surgeon has angular directional control as to where bone graft material is directed. Other detachable elements are also contemplated with the present invention, such as a funnel at the proximal end of the hollow tube, or exterior or interior guide wires attached to the hollow tube, or a camera which is positioned near the delivery site of the bone graft material.

In another embodiment of the invention, the device is configured such that the upper or first end of the device (that is, the end in which the plunger is inserted) is not substantially in-line with the second end of the device (that is, the end from which bone graft material is emitted and/or a fusion cage is attached). For example, the body of the hollow tube may be configured with an angle or kink along its length, appearing to be rotated along its length. In this embodiment, the plunger element is flexible and/or conformable so as to flex inside of the tube portion and otherwise traverse through the tube portion. This embodiment of the device is useful, for example, when the user requires entry to the disc space at other than a right angle. Further, the angle or kink along the length of the device may be configured is capable of selectively locking (e.g., by a pin) the upper device portion into a particular position, e.g. so that a desired angle is created between the upper device portion and the remaining portion of the device. The means for communication itself can be locked to alternatively achieve this objective. In one embodiment, when the rotating member is in an unlocked mode, the member is free to rotate in at least one plane. The selective locking mechanism can be remotely accessed by a user of the tool at the upper end of the handle by, for example, an external shaft that communicates with the locking mechanism of the rotating member on the distal end of the body. Yet another aspect of the present disclosure is that the device can be variably angled to allow for a variety of insertion angles. A ratcheting adapter can be fitted to allow for this application.

The present invention can be used in veterinary conditions, in the thoracic spine or can be used for insertion of a laterally based disk replacement.

Thus, according to various embodiments of the present disclosure, a method of introducing bone graft material to a desired operating site ("bone graft receiving area") is provided by use of a hollow tubular member comprising a generally rectangular cross-sectional area, whereby the desired operating area is capable of receiving at least one plunger. The one or more plunger having at least one distal end which is designed to accommodate ejecting bone graft or other material to be inserted into the joint space or between intervertebral members in a generally lateral direction, as opposed to a generally longitudinal direction (in relation to the direction of the primary axis of the device).

One skilled in the art will appreciate that the distal end of the tubular device need not be limited to those specific embodiments described above. Other forms, shapes or designs that enable the foregoing aspects of the present invention are hereby incorporated into this disclosure. Forms, shapes and designs that relate to the provision of an end of a tubular device to perform lateral introduction of bone or bone substitute to an operating site are considered to be within the scope of the present disclosure.

One aspect of the present invention provides an integrated fusion cage and graft delivery device system for delivering bone graft, in a partially formed, fully formed or unformed condition to a bone graft receiving area in a body.

In yet another embodiment the hollow tube of the integrated fusion cage and graft delivery device may further comprise a funnel on the graspable end of the hollow tube, which may be selectively positioned about the graspable end of the hollow tube, for facilitating insertion of new or additional bone graft into the hollow tube. The funnel may take on a variety of shapes and sizes, depending on the nature of the bone graft material being inserted in the hollow tube.

One embodiment of the substantially hollow tube provides that the hollow tube is telescoping, thereby allowing its length to be adapted to the particular desires of the surgeon and/or the surgical area. In this embodiment, the plunger may also be telescoping to substantially conform to the configuration and/or size and/or shape of the substantially hollow tube.

In another embodiment, the size and/or shape of the one or more hollow tubes of the device are sized to fit, and/or not substantially obscure access to the aperture of, the cannula or cannulas that the device is fitted through for delivery of bone graft material to the operating site. In this embodiment, the device's one or more pair of hollow tubes and plungers do not substantially impair access to the operating site nor the surgeon's view of the operating site.

In one embodiment of the invention, a bone graft insertion apparatus comprises: a hollow tube constructed to receive bone graft, said hollow tube having an extended axis and a proximal end and a distal end, said distal end having an interior surface; a plunger adapted for inserting into said proximal end of said hollow tube, said plunger having a distal end being contoured to said interior surface of said distal end of said hollow tube such that bone graft material within said hollow tube is delivered to a graft receiving area through at least one opening near the distal end of said hollow tube; wherein said graft receiving area is configured to accommodate at least one substantially hollow implant.

In another embodiment of the invention, a bone graft insertion apparatus comprises: a hollow tube constructed to receive bone graft, said hollow tube having a proximal and distal end; whereby said hollow tube contains least one opening on a surface of said distal end of said hollow tube; whereby said opening on a surface of said distal end of said hollow tube is positioned other than completely along the axial or longitudinal axis of the device; a plunger adapted for insertion at least partially within said hollow tube at proximal end of said hollow tube; whereby said plunger is constructed and arranged with respect to said hollow tube so as to present at least one substantially flat contour; whereby said plunger has a distal end that is contoured to an interior surface of said distal end of said hollow tube such that said contoured distal end of said plunger is nearly congruent with said interior surface of said distal end of said hollow tube for removing substantially all of said bone graft received by said hollow tube; whereby said bone graft is delivered to a graft receiving area.

In another embodiment of the invention, a method of inserting bone graft comprises: preparing a surgical area to receive bone graft; inserting a tool into said surgical area, said tool consisting essentially of a hollow tube adapted to receive bone graft, a plunger adapted for insertion into said hollow tube, said plunger constructed to prevent rotation during insertion into said hollow tube, said plunger having a distal end contoured to the interior surface of the distal end of said hollow tube; providing bone graft material into the said hollow tube of said tool; inserting said plunger into the proximal end of said hollow tube; inserting said distal end of said hollow tube of said tool into surgical area; applying force to said plunger thereby advancing said plunger through said hollow tube wherein said bone graft is inserted into said surgical area.

In another embodiment of the invention, an integrated fusion cage and graft delivery device apparatus comprises: a hollow tube constructed to receive bone graft, the hollow tube having an extended axis and a proximal end and a distal end, the distal end having an interior surface; a plunger adapted for inserting into the proximal end of the hollow tube, the plunger having a distal end being contoured to the interior surface of the distal end of the hollow tube; a selectably detachable fusion cage, the selectably detachable fusion cage having at least one opening that substantially aligns with at least one opening near the distal end of the hollow tube, such that bone graft material within the hollow tube is delivered to a graft receiving area through at least one opening of the selectably detachable fusion cage; and the selectably detachable fusion cage having a means for detachment whereby the fusion cage is delivered to the graft receiving area.

In one embodiment, the device is not a caulking gun style device, that is the bone graft material and/or the fusion cage are not delivered and/or positioned using a hand-pump and/or hand-squeeze mechanism. Instead, the device delivers graft material and/or a fusion cage using a hollow tube and plunger arrangement which is not a caulking gun style device and further, does not appreciably disrupt or block the user's view of the surgical site and/or enable precision delivery of bone graft material and/or a fusion cage to the surgical site. Indeed, the device is distinctly unlike the chalking gun device of U.S. Pat. Appl. No. 2004/0215201 to Lieberman ("Lieberman"), which requires an L-shaped base member handle, rack teeth to advance a plunger member, and user action on a lever of the L-shaped base member handle to deploy bone graft material. In one embodiment, the device of this application is not a caulking gun style device and does not comprise rack teeth, a base member handle and at least one component that obscures user viewing of the surgical site. Lieberman is incorporated by reference in its entirety for all purposes.

Similarly, in one embodiment, the device is distinctly unlike the chalking gun device of U.S. Pat. Appl. No. 2002/0049448 to Sand et al ("Sand"), which requires a gun and trigger mechanism in which the user squeezes together a gun-style handle to deploy material into bone. The Sand device obstructs the view of the user of the delivery site. In one embodiment, the device of this application is not a caulking gun style device and does not comprise an opposing-levered, gun-style delivery mechanism and at least one component that obscures user viewing of the surgical site. Sand is incorporated by reference in its entirety for all purposes.

In one embodiment, the device is configured to deliver bone graft material substantially laterally from its delivery end, that is substantially not in the axial direction but rather substantially from the side and/or in a radial direction. This is distinctly different than devices that deliver bone graft material along their vertical axis, that is, along or out their bottom end, and/or obstruct the user view of the bone graft and/or fusion cage delivery site, such as that of U.S. Pat. Appl. No. 2010/0087828 to Krueger et al ("Krueger"), U.S. Pat. Appl. No. 2009/0264892 to Beyar et al ("Beyar"), U.S. Pat. Appl.

No. 2007/0185496 to Beckman et al ("Beckman"), U.S. Pat. Appl. No. 2009/0275995 to Truckai et al ("Truckai") and U.S. Pat. Appl. No. 2006/0264964 to Scifert et al ("Scifert"). Krueger, Beyar, Beckman, Truckai and Scifert are incorporated by reference in their entireties for all purposes.

In one embodiment, the device is configured to deliver bone graft material so as to completely fill the defined interior of its fusion cage and subsequently deliver bone graft material to the surrounding bone graft site, rather than, for example, to contain the bone material as are the fusion cage designs of U.S. Pat. No. 7,846,210 to Perez-Cruet ("Perez-Cruet"). Further, the fusion device of this application features a distal tip that functions to precisely position the fusion device and stabilize the device during delivery of bone graft material. Perez-Cruet is incorporated by reference in its entirety for all purposes.

One of ordinary skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. The plunger element could be flexible, semi-rigid, or rigid and made of materials such as stainless steel, titanium alloy, aluminum alloy, chromium alloy, and other metals or metal alloys. Similarly, the tubular element could be flexible, semi-rigid, or rigid and made of materials such as stainless steel, titanium alloy, aluminum alloy, chromium alloy, and other metals or metal alloys. In certain embodiments, the plunger and hollow tube are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the hollow tube and/or plunger are made of a substantially transparent material and/or are rigidly opaque.

In one embodiment of the fusion cage, the fusion cage comprises a polymer, such as PEEK, titanium and composite materials.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the speed of the procedure, the minimally invasive aspect of the procedure, the ability to introduce the implant material to the implant site with minimal risk and damage to the surrounding tissue, the lower risk of infection, more optimally placed implant material, a more stable delivery device which is designed to reduce the likelihood of the implant material becoming dislodged prior to fixation, and fewer tools in a surgical site due to the integration of several components required to provide bone graft to a bone graft receiving area. Further, the lower profile of the device allows improved viewing of the area intended for receipt of bone graft material, and use of a reduced set and size of elements therein provided a less expensive device. Also, the device disclosed provides that substantially all of the bone graft material may be ejected from the device and delivered to the surgical site, rather than wasted as unretrievable matter remaining inside the device. The ability to remove substantially all of the bone graft material is of significant benefit because the bone graft material is expensive and/or hard to obtain.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

The present invention relates to a device and method for integrated and near-simultaneous delivery of bone graft material and a fusion cage to any portion of a patient which requires bone graft material and/or a fusion cage. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The integrated fusion cage and graft delivery device is formed such that the one or more hollow tubes and/or plungers may be helpful in selectively and controllably placing bone graft material and a fusion cage in or adjacent to such window. The integrated fusion cage and graft delivery device is formed to allow delivery of bone graft material and/or a fusion cage in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present invention also contemplates the delivery of bone graft material and/or a fusion cage with or without the use of a plunger, and with or without the use of various other tools described in greater detail herein.

Referring now to FIGS. 1-17, several embodiments of the present invention are shown.

Figure 1A:
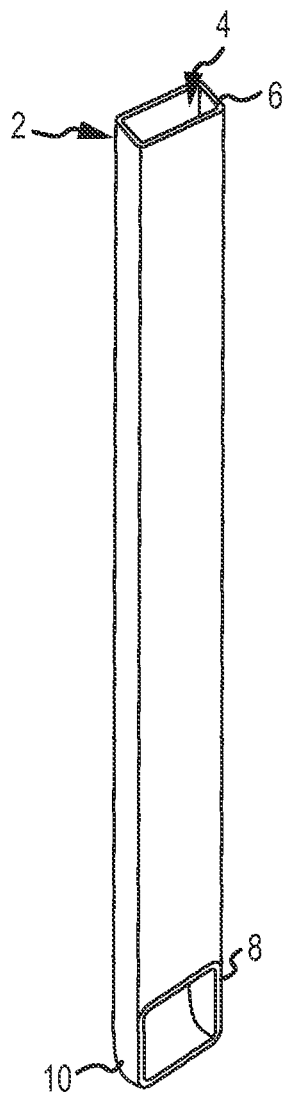
FIG. 1A is a perspective view of the device for delivering bone graft.

In regard to FIG. 1A, an integrated fusion cage and graft delivery device portion is shown, which is comprised of a hollow tubular member or hollow tube or contains at least one inner lumen 2, which has a first proximate end 6 (which is referred to elsewhere in this specification as the "graspable end" of hollow tube 2), and a second distal end 8, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the second end 8. According to a preferred embodiment, the hollow tube 2 also comprises at least one sloped or curved surface 10 at or near the second end 8 of the hollow tube 2. Although a generally rectangular cross-section is depicted, the cross-section need not be limited to a generally rectangular shape. For example, cross-sections of an oval shape or those with at least one defined angle to include obtruse, acute, and right angles can provide a shape in some situations that is more congruent with the size or shape of the annulotomy of a particular disc space.

Figure 1B:
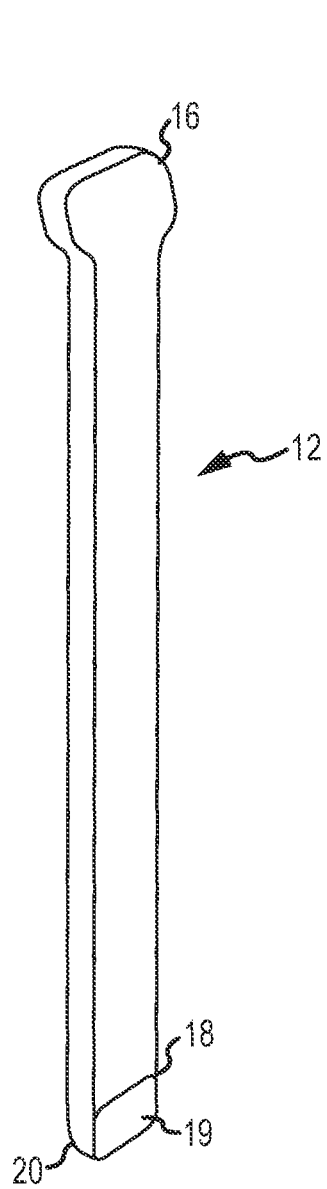
FIG. 1B is a perspective view of the plunger of the device.

Referring now in detail to FIG. 1B, a plunger 12 is shown for use with the hollow tube 2 of FIG. 1A. The plunger 12 is generally of the same geometry as the hollow potion of the hollow tube 2, extending at least the same length of hollow tube 2. The plunger 12 may includes, as depicted in FIG. 1B at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat, horizontal surface 19, which corresponds to the opening at the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the horizontal surface 19 of plunger 12 is in communication with the second end 8 of the hollow tube 2. This configuration permits a user to eject substantially all of the bone graft material that is placed into the hollow tube 2 during a surgical procedure. One skilled in the art will appreciate that the plunger need not terminate in a generally flat, horizontal surface to effect the substantial removal of all of the bone graft material placed into the hollow tube; more specifically, any shape that allows conformance between the internal contour of the distal end of the hollow tube and the distal end of the plunger will effect the substantial removal of the bone graft material. Further details about the relationship are described below in regard to FIG. 2.

Figure 1C:
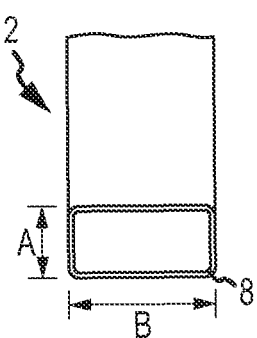
FIG. 1C is a cross sectional view of a portion of the device shown in FIG. 1A.

In the embodiment, of FIG. 1A-C, a contoured leading edge is provided on the plunger to correspond with the internal contour of distal end of the hollow tube of the delivery device. This contoured plunger serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensure that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. Alternative positioning means may also be provided to ensure that the plunger remains in the desirable position during delivery of bone graft into the hollow tube, for example by a machined bevel or edge on the outer surface of the plunger, and a corresponding groove in the interior surface of the hollow tube, which must be aligned when inserting the plunger in the hollow tube.

Referring now to FIG. 1C, an elevation view of the hollow tube 2 shown in FIG. 1A is shown in detail. The second end 8 of the hollow tube 2 has an opening with a height A and width B according to the needs of the surgeon, the location of the bone graft receiving area, the nature of the surgical operation to be performed, and the quantity and type of bone graft that is being inserted in (and ultimately ejected from) this integrated fusion cage and graft delivery device. According to a preferred embodiment, the height A of the opening at the second end 8 of the hollow tube 2 is in the range of 4 mm to 9 mm, and in a most preferred embodiment is about 7 mm. According to a preferred embodiment, the width B of the opening at the second end 8 of the hollow tube 2 is in the range of 7 mm to 14 mm, and in a most preferred embodiment is about 10 mm.

Referring to FIGS. 1A-C, it is to be understood that although these particular drawings reflect an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, that in other embodiments, the second end 8 of the hollow tube 2 (and thereby, the second end 18 of the plunger 12) do not extend a lateral distance away, but rather terminate along the longitudinal wall of the hollow tube 2. In this embodiment, the hollow tube 2 may have a second end 8 which has an opening that is carved out of the side of the wall of the hollow tube 2, such that it appears as a window in the tubular body of hollow tube 2. According to this embodiment, the horizontal face 19 of the plunger 12 would also be a face on the outer surface of plunger 12, without extending any lateral distance away from the body of plunger 12. According to this embodiment, the plunger 12 would still retain the curved or sloped surface at the opposite end of the horizontal face 19 (referred to in FIG. 1B as 20) and similarly the hollow tube 2 would still comprise a sloped or curved surface 10 opposite the opening at second end 8. It is to be expressly understood that other variations which deviate from the drawing FIGS. 1A-C are also contemplated with the present invention, so long as that the opening at the second end 8 of hollow tube 2 is oriented to permit bone graft to be exited from the hollow tube 2 in a generally lateral direction (in relation to the longitudinal direction of the axis of the hollow tube 2).

According to another embodiment, the plunger 12 shown in FIG. 1B may further comprise a secondary handle (not shown in FIG. 1B), which includes an opening about at least one end of secondary handle such that it is permitted to couple with handle 16 of plunger 12. In this fashion, the secondary handle may be larger, contain one or more rings or apertures for placing a users hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Figure 2:
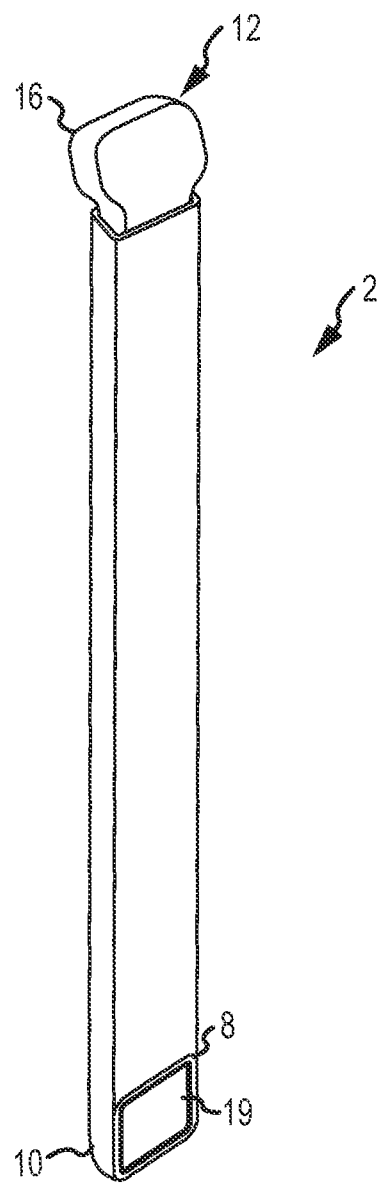
FIG. 2 is another perspective view of the device of FIGS. 1A-C, showing the relationship between the tubular and plunger portions of the device of FIG. 1.

Referring now in detail to FIG. 2, the plunger 12 is shown inserted into the hollow tube 2, such that the horizontal face 19 is substantially planar with the opening at the second end 8 of the hollow tube 2. As described above, the geometry of plunger 12 is such that it fits snuggly or tightly in the interior of the hollow tube 2. This configuration is such that the sloped or curved surface 10 of the hollow tube 2 is substantially congruent to the sloped or curved surface 20 (not shown in FIG. 2), thereby allowing the plunger to be inserted into the hollow tube 2 and allowing substantially all of bone graft material which is placed into the hollow tube 2 to be ejected by the user.

Figure 3:
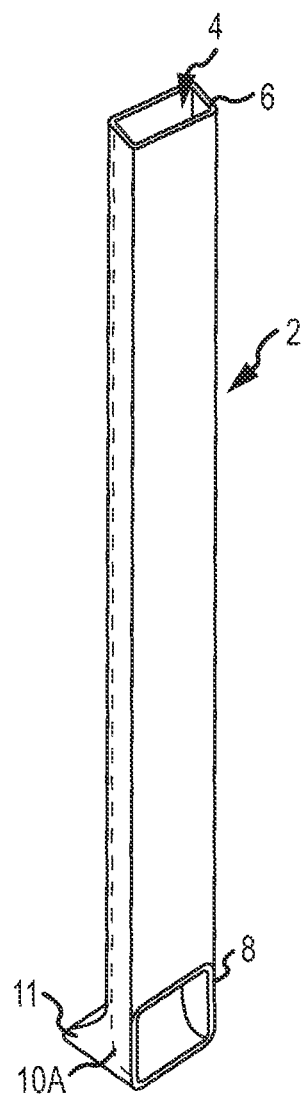
FIG. 3 is a perspective view of the device according to one alternative embodiment where the tubular portion includes a foot section and where the plunger portion has been fully inserted into the tubular portion.

Referring now in detail to FIG. 3, an alternate embodiment of the present invention is shown. According to this embodiment, the hollow tube 2 comprises a footing 11 at the second end 8 of the hollow tube 2. This footing 11 extends in a lateral direction, opposite the direction of the opening at the second end 8 of the hollow tube 2. The purpose of this footing 11 is to prevent injury to the annulus of a patient, or other sensitive anatomy adjacent the bone graft receiving area. This footing 11 is helpful when a surgeon or other user of the integrated fusion cage and graft delivery device is using the plunger 12 to drive bone graft through the hollow tube 2, or using another tool, such as a tamp, mallet, or other driving or impacting device to strike the plunger 12 and/or hollow tube 2 during the surgical procedure. Without the footing 11, the hollow tube 2 would have a generally angular second end 8, which may cause damage to the patient during these types of procedures. Thus, the footing 11 prevents the second end 8 of the hollow tube 2 from penetrating the annulus or other sensitive anatomy of the patient.

According to this embodiment, the footing 11 may also operate to ensure a fixed position of the second end 8 of the hollow tube 2 in the surgical site. This in turn allows a user to ensure that bone graft ejecting the second end 8 of the hollow tube 2 is being ejected laterally, and in the desired direction. This may be important, for example, when the integrated fusion cage and graft delivery device is placed within a disc space, and bone graft is being ejected laterally from the second end 8 of the hollow tube 2 in a specific direction. In other embodiments, the footing 11 may also serve as a visual marker for the surgeon, as it extends away from the horizontal wall of the hollow tube 2, and is therefore visible at the second end 8 of the hollow tube 2. As shown in FIG. 3, the presence of the footing 11 does not affect the interior slope or curved surface 10A of the hollow tube 2, so that the plunger 12 of the design shown in FIG. 1B may still be used with the hollow tube 2 of this alternate embodiment.

Figure 4:
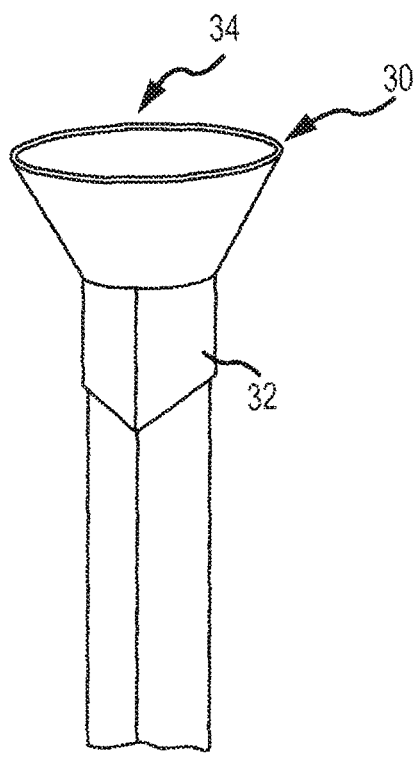
FIG. 4 is a partial perspective view of another alternative embodiment where the tubular portion includes a funnel at its proximal end designed to receive bone graft.

Referring now in detail to FIG. 4, a removable funnel 30 is shown, which comprises an opening 34 which is generally larger in diameter or dimension when compared to the opening 4 of the hollow tube 2. This removable funnel 30 further comprises a sleeve 32, the sleeve 32 having an internal cross-section which is substantially congruent with the external cross-section of the first end 6 of the hollow tube 2. Thus, according to this embodiment, the funnel 30 is selectively removable from the first end 6 of the hollow tube 2, and may allow a surgeon to more easily place new or additional bone graft into the hollow tube 2 by way of the opening 34 of the funnel 30. This funnel 30 may be used in connection with a hollow tube 2 that has been pre-filled with bone graft, or a hollow tube which is not pre-filled with bone graft. Thus, the funnel may be selectively positioned on the first end 6 of the hollow tube 2 at any point during the surgical operation when the surgeon desires new or additional bone graft be placed in the hollow tube 2 of the integrated fusion cage and graft delivery device.

Figure 5:
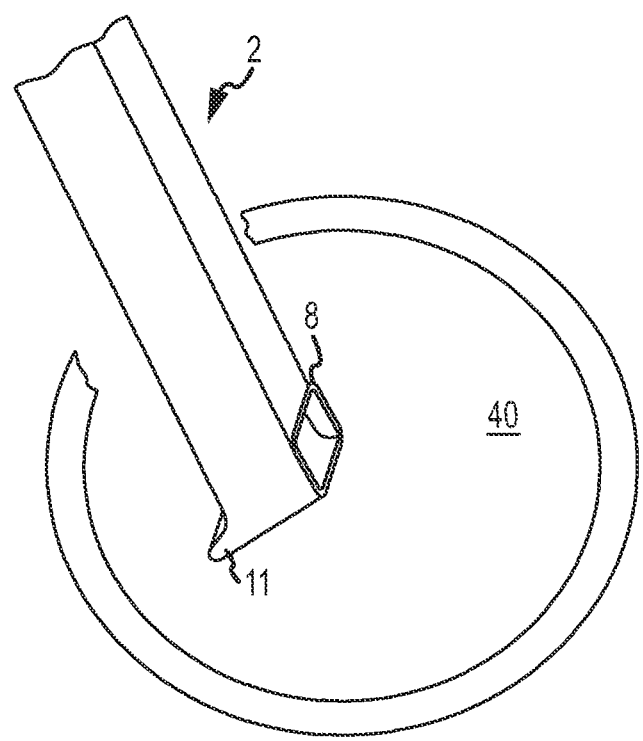
FIG. 5 is a perspective view of the device according to one embodiment where the device is positioned in a disc space during a surgical operation.

Referring now in detail to FIG. 5, one particular application of the integrated fusion cage and graft delivery device is shown in a perspective view. Here, the integrated fusion cage and graft delivery device is shown with the embodiment of the hollow tube 2 further comprising a footing 11, and a second end opening for ejecting bone graft in a generally lateral direction, here in the interior of a disc space 40. The disc is shown with an opening on one end for inserting the second end 8 of the hollow tube 2 of the integrated fusion cage and graft delivery device. As opposed to prior art integrated fusion cage and graft delivery devices which have an opening at a second end that is open to the longitudinal axis of the delivery device, the present invention comprises a lateral opening, which as shown in FIG. 5 allows a surgeon to eject bone mill into the lateral direction and thereby into the opened areas of the disc space 40. A surgeon has the option to rotate the direction of the opening in the second end 8 of the hollow tube 2 for ejecting additional bone graft to other open areas in the disc space 40. Once the disc space 40 is substantially full of bone graft, the surgeon may remove the hollow tube 2 without disturbing the disc or anatomy of the patient. The surgeon may also accomplish the delivery of bone graft without displacing any cage or other structural implantable device which may be present in or adjacent the disc space. One skilled in the art will appreciate that the hollow tube 2 further comprising a footing 11, and a second end opening for ejecting bone graft in a generally lateral direction, may effect the delivery of bone graft in a lateral direction simultaneous with delivery in a longitudinal direction.

Figure 6:
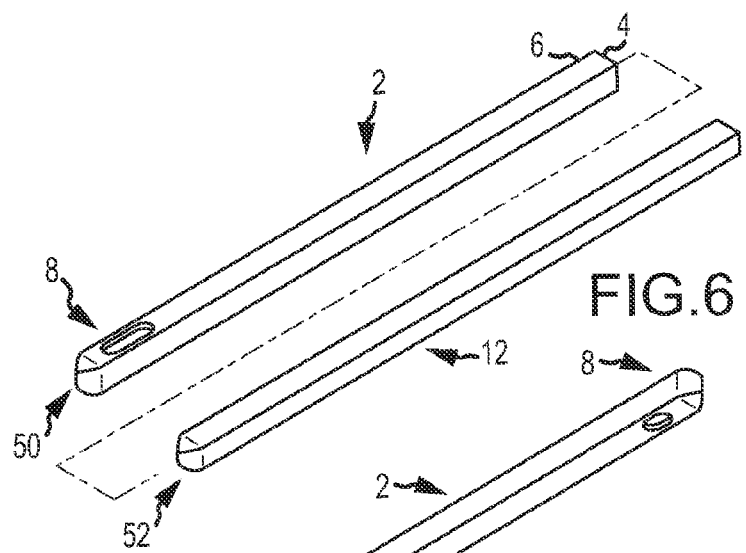
FIG. 6 is a perspective view of one embodiment of the device, showing the relationship between the tubular and plunger portions where the tubular portion includes two lateral facing openings at the distal end of the tubular portion and a wedge-shaped distal end of the tubular member.

Referring now to FIGS. 6-10, a preferred embodiment of the device is shown. In regard to FIG. 6, a integrated fusion cage and graft delivery device portion is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable (the other is viewable in FIG. 7). Also in FIG. 6, the plunger member 12 is shown. The manner of insertion of plunger member 12 into tubular member 2 is also provided. Thus, as shown in FIG. 6, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2.

Furthermore regarding FIG. 6, a preferred embodiment of the distal end 10 of the tubular member 2 and the distal end 20 of the plunger member 12 is provided. The configuration provided, a wedge-shaped end 50 of the tubular member and a wedge-shaped end of the plunger 52, allows substantially all of the bone graft material to be removed and thus inserted into the surgical area when the plunger 2 is fully inserted into the tubular member 2. The wedge-shaped feature 50 of the distal end 10 of the tubular member 2 and the wedge-shaped end 52 of the distal end 20 of the plunger member 12 is discussed in additional detail with respect to FIGS. 8 and 9 below. The ability to remove substantially all of the bone graft material is an important feature of the invention because bone graft material is traditionally expensive and may require surgery to obtain.

Figure 7:
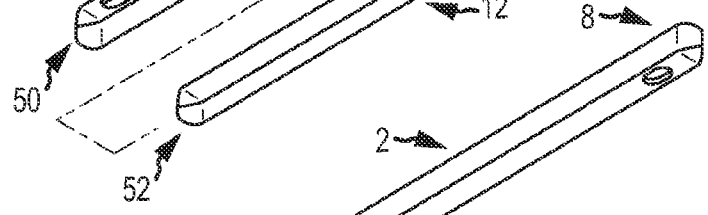
FIG. 7 is a another perspective view of the tubular portion of the device of FIG. 6 showing the second of two lateral openings at the distal end of the tubular portion and a wedge-shaped distal end of the tubular member.

Referring now to FIG. 7, a perspective view of a preferred embodiment of the hollow tubular member 2 is provided. Consistent with FIG. 6, the generally hollow tube 2 is shown with one of two lateral openings at the distal end 8 of the tubular member 2 viewable (the other is viewable in FIG. 6). Thus, in operation the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2. In this configuration, bone graft material is ejected into the surgical area in two lateral directions. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Figure 8:
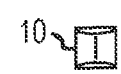
FIG. 8 is an elevation view of the of the distal end of the tubular portion of the device.

Referring now to FIG. 8, an elevation view of the wedge-shaped distal end 50 of the tubular member 2 is provided. In this embodiment, the proximal end of the plunger would conform to the same shape, to allow close fitting of the plunger and the hollow tubular member. This contoured plunger, corresponding to the contoured tubular member, serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensure that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. One skilled in the art will appreciate that the plunger need not terminate in a wedge-shape surface to effect the substantial removal of all of the bone graft material placed into the hollow tube; more specifically, any shape that allows conformance between the internal contour of the distal end of the hollow tube and the distal end of the plunger will effect the substantial removal of the bone graft material.

Figure 9:
FIG. 9 is an elevation view of the proximal end of the tubular device.

Referring now to FIG. 9, an elevation view of the opening 4 of the distal end 6 of the hollow tubular member 2 is provided. As shown in FIG. 9, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, cross-sections of an oval shape or those with at least one defined angle to include obtruse, acute, and right angles can provide a shape in some situations that is more congruent with the size or shape of the annulotomy of a particular disc space.

Figure 10A:
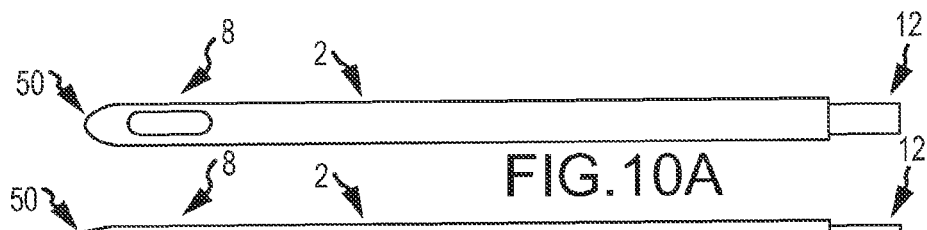
FIG. 10A-D are sequential elevation views of the device with the plunger portion fully inserted into the tubular portion.
Figure 10B:
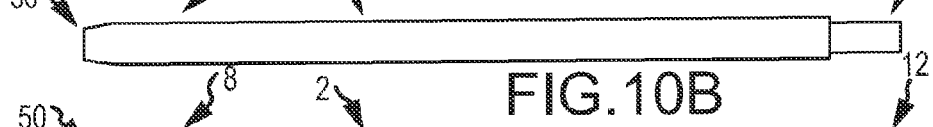
Figure 10C:
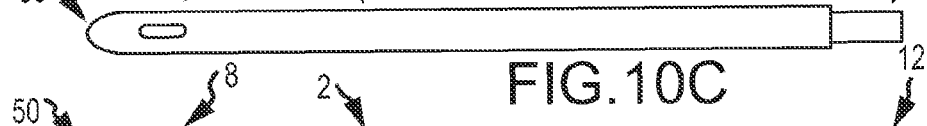
Figure 10D:
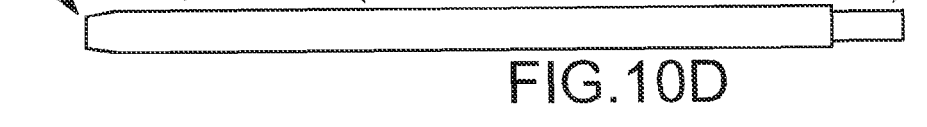
Figure 11A:
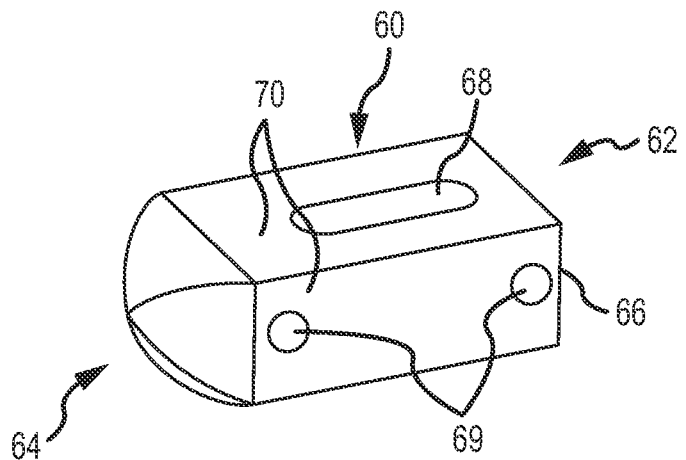
FIG. 11A-D are views of one embodiment of the fusion cage of the device, showing a tapered proximal end and medial openings.
Figure 11B:
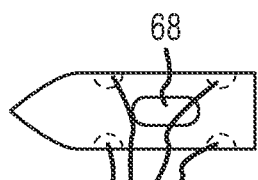
Figure 11C:
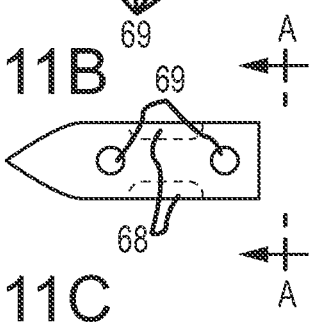
Figure 11D:
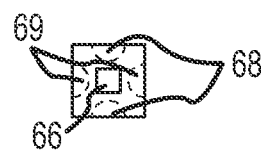

Referring to FIGS. 10A-D, sequential elevation views of the square-shaped embodiment of the integrated fusion cage and graft delivery device 1 are provided, depicting the complete insertion of the plunger 12 into the hollow tubular member 2. In each of FIGS. 10A-D, the wedge-shaped distal end 50 of the tubular member 2 is depicted. Also, each of FIGS. 10A-D depict the additional length of the plunger element 12 when inserted into the tubular member 2. FIG. 10A shows one of two lateral openings at the distal end 8 of the hollow tubular member 2. FIG. 10C shows another of the two lateral openings at the distal end 8 of the hollow tubular member 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Referring to FIGS. 11A-D, a fusion cage 60 of an integrated fusion cage and graft delivery device 1 portion is shown, which is comprised of a integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may comprise one or more medial openings 68 that align with one or more openings at the distal end 8 of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted in to the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 and/or the bone graft delivery portion of the integrated fusion cage and graft delivery device is of oblong or rectangular or square shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

In a preferred embodiment, the fusion cage 60 has a keel-shaped tip to separate disk and prevent annular penetration. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 12A:
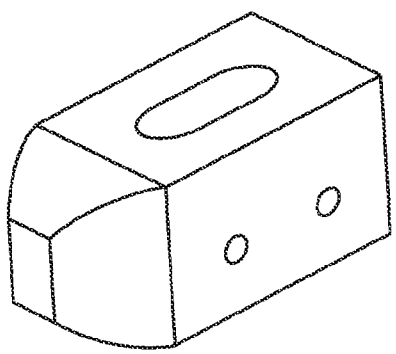
FIG. 12A is a front perspective view of another embodiment of the fusion cage of the device.
Figure 12B:
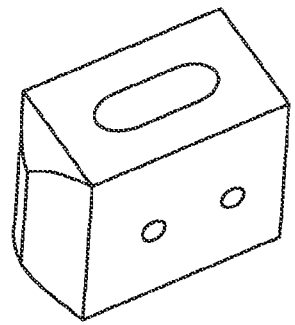
FIG. 12B is a front perspective view of yet another embodiment of the fusion cage of the device.
Figure 12C:
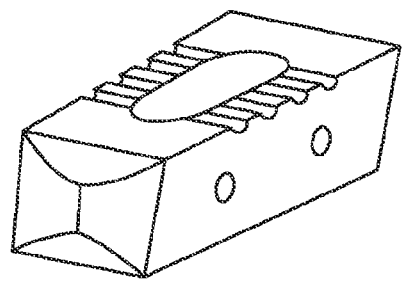
FIG. 12C is a front perspective view of yet another embodiment of the fusion cage of the device.

Referring now to FIGS. 12A-C, two alternate embodiments of the fusion cage 60 are provided. FIG. 12A shows an embodiment of the integrated fusion cage 60 with a second distal end 64 tapered to a flat rectangular shape end. FIG. 12B shows an embodiment of the integrated fusion cage 60 with a second distal end 64 tapered to a wedged-shaped end. Such a configuration would be, for example, would be conformal with the wedge-shaped second end 50 of the hollow tube 2, as shown in FIGS. 6-8. FIG. 12C shows an embodiment of the integrated fusion cage 60 with belts of striations imparted to the upper medial surface 70 of the fusion cage 60.

Figure 13:
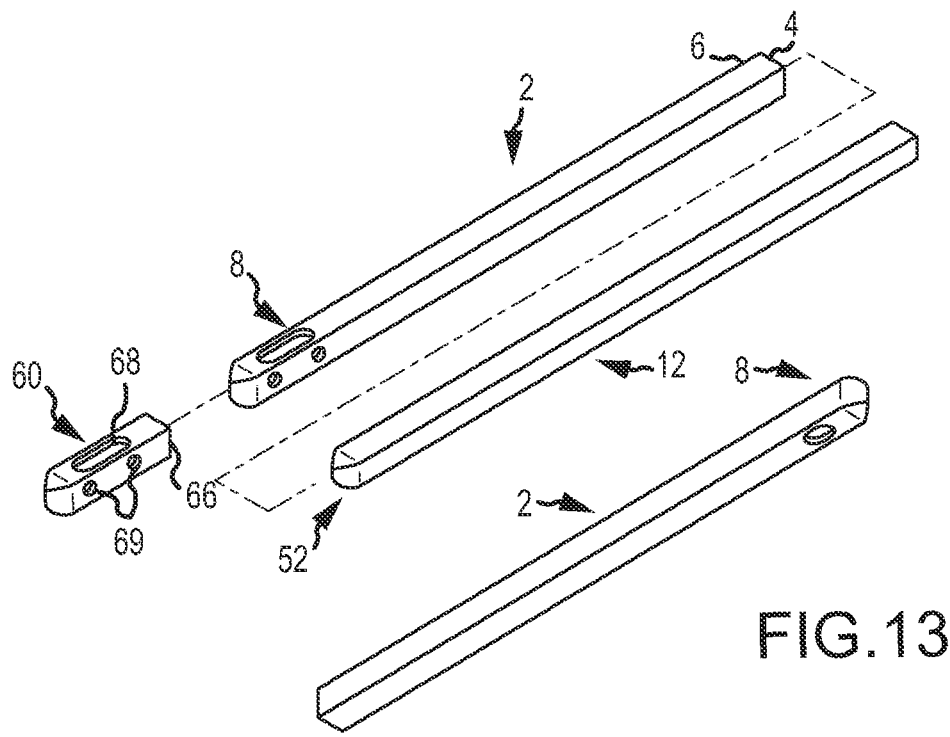
FIG. 13 is a perspective view of one embodiment of the device, showing the relationship between the tubular and plunger portions where the tubular portion includes two lateral facing openings at the distal end of the tubular portion and a wedge-shaped distal end of the tubular member, and a fusion cage fitting over the exterior distal end of the tubular member, wherein the fusion cage has medial openings.
Figure 14A:
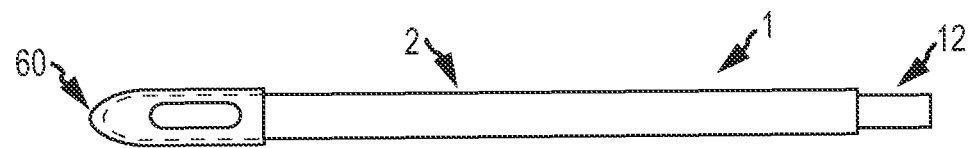
FIG. 14A-D are sequential elevation views of the device with the plunger portion fully inserted into the tubular portion and the fusion cage fully inserted over the tubular portion.
Figure 14B:
Figure 14C:
Figure 14D:
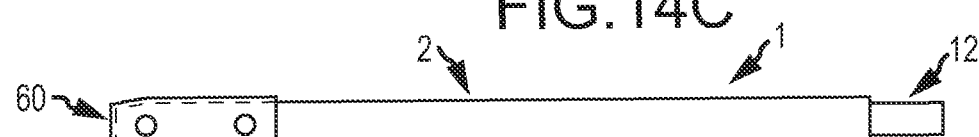

In regard to FIG. 13, an integrated fusion cage and graft delivery device 1 is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable. Also in FIG. 13, the plunger member 12 is shown and the fusion cage 60. The manner of insertion of plunger member 12 into tubular member 2 is also provided, as is the manner of insertion of fusion cage 60 over tubular member 2 and into the fusion cage first end opening 66. Thus, as shown in FIG. 13, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2 and through the medial openings 68 and/or the lateral openings 69 of the fusion cage 60.

Referring to FIGS. 14A-D, sequential elevation views of the square-shaped embodiment of the integrated fusion cage and graft delivery device 1 are provided, depicting sequential elevation views of the integrated fusion cage and graft delivery device 1 with the plunger portion 12 fully inserted into the tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral and medial openings may vary, for example the distal end 8 of the tubular member 2 may have more than two openings that are of different shape (e.g. oval, rectangular).

Referring to FIGS. 15A-D, a fusion cage 60 of an integrated fusion cage and graft delivery device portion is shown, which is comprised of a integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted in to the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 is of a square shape and the bone graft delivery portion of the integrated fusion cage and graft delivery device is of a cylindrical shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

Figure 15A:
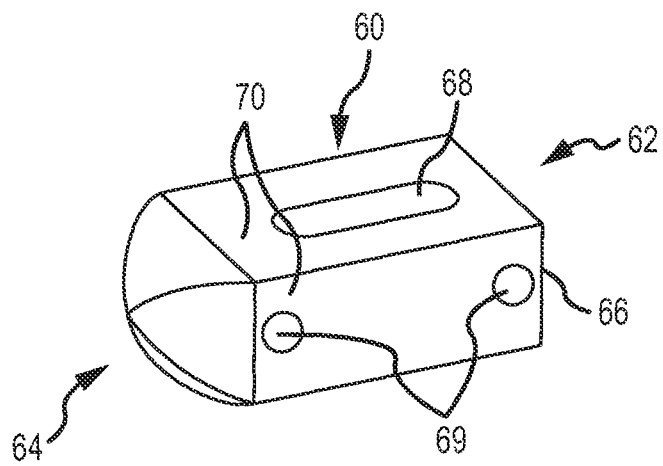
FIG. 15A-D are views of another embodiment of the device wherein the fusion cage includes internal ramps and locking slots and wherein the tubular portion includes locking tabs.
Figure 15B:
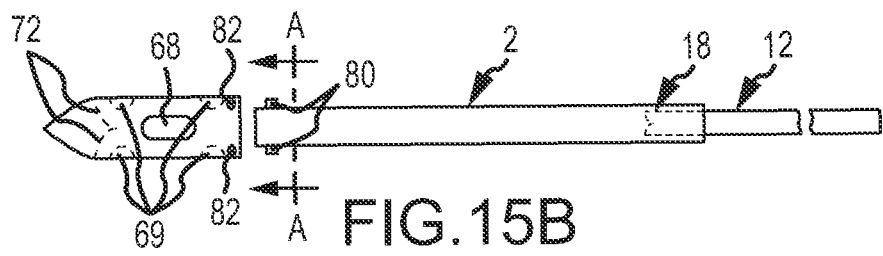

In a preferred embodiment, the fusion cage 60 has a keel-shaped tip to separate disk and prevent annular penetration and has internal ramps 72 which assist in directing the bone graft material to one or more lateral openings 69. As the plunger 12 is inserted into the hollow tube 2, bone graft material is directed by the fusion cage internal ramps 72 out the lateral openings 69, and bone additionally bone graft material may flow out the one or more medial openings 68. The plunger end 18 may be configured to be conformal with the internal ramps 72 of the fusion cage 60, as depicted in FIG. 15B. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 15C:
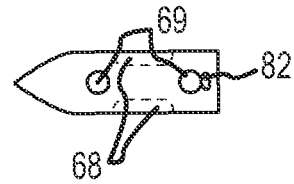
Figure 15D:
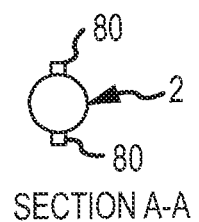

In a preferred embodiment as shown in FIGS. 15B-D, the hollow tube 2 is of cylindrical shape and includes one or more locking tabs 80 configured to engage one or more locking slots 82 of the fusion cage 60. The locking tabs 80 may permanently or not permanently engage the locking slots 82, and may be of shape to include rectangular, circular and oblong. The instruments used with the integrated fusion cage and graft delivery device described above in its varying embodiments may include one or more tamps, preferably having a configuration which at least in part corresponds in shape and contour of the hollow tube portion of the delivery device. The one or more tamps may be adapted to correspond further to the shape and contour of the graspable end of the plunger, for use in driving the plunger through the hollow tube portion of the delivery device to ensure any remaining bone graft located in the hollow tube is delivered to the graft receiving area.

Figure 16:
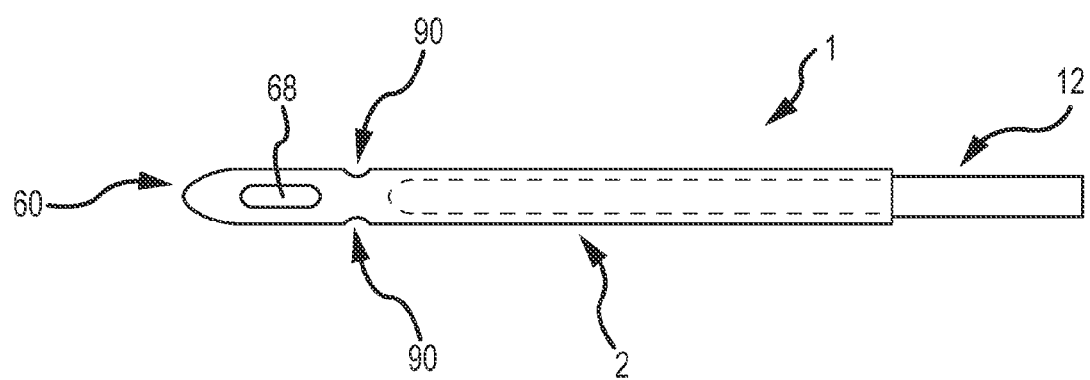
FIG. 16 is an elevation view of another embodiment of the device with the plunger portion partially inserted into the tubular portion and the fusion cage engaged with the tubular portion via a break-off collar.

In the embodiment of the device of FIG. 16, the hollow tube 2 engages with the fusion cage 60 via a break-off collar 90 and the plunger 12 inserts into the interior of the hollow tube 2. The plunger 12 is depicted partially inserted into the hollow tube 2. The break-off collar 90 may be severed by any of several means, to include application of torsion and/or rotational force and/or lateral force to break-off collar 90, for example by twisting on the hollow tube 2 and/or the plunger 12.

Figure 17A:
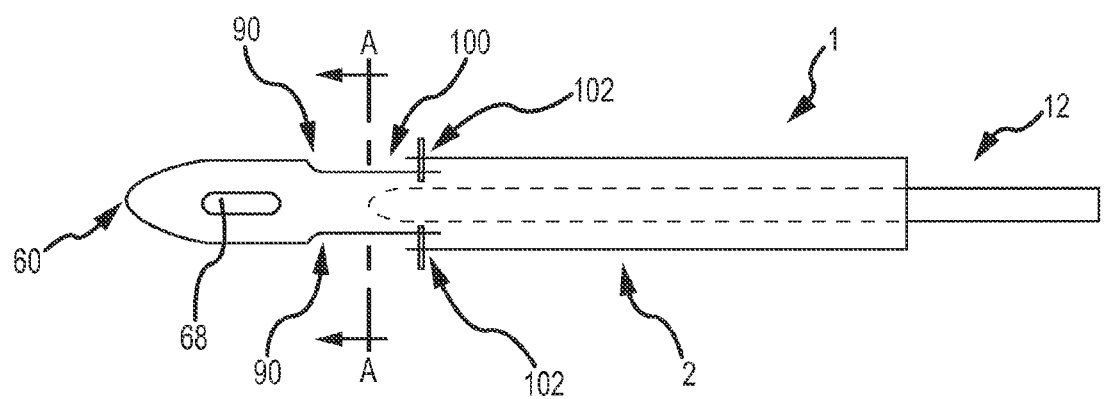
FIG. 17A-B are views of another embodiment of the device wherein the fusion cage engages with a connector conduit which in turn engages with the tubular portion.
Figure 17B:
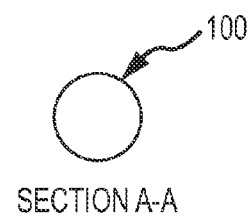
Figure 18A:
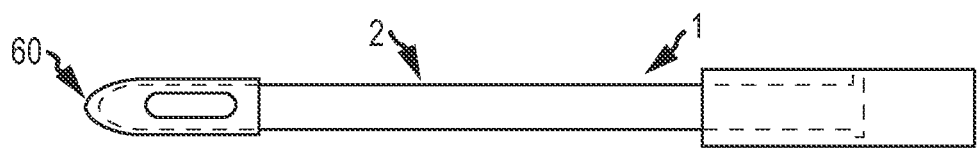
FIG. 18A is a top plan view of another embodiment of the device wherein the tubular portion comprises a telescoping feature.
Figure 18B:
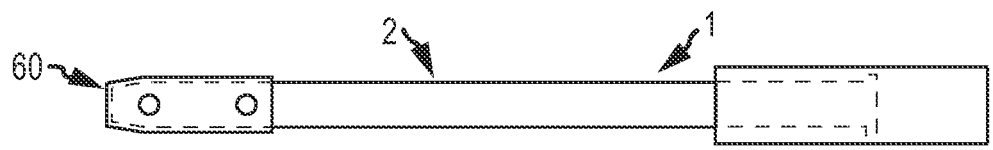
FIG. 18B is a left elevation view of the device of FIG. 18A.
Figure 18C:
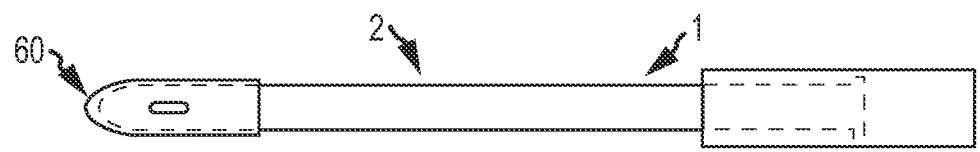
FIG. 18C is a bottom plan view of the device of FIG. 18A.
Figure 18D:
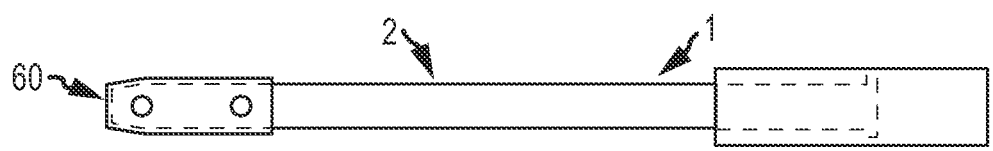
FIG. 18D is a right elevation view of the device of FIG. 18A.

In the embodiment of the device of FIG. 17A-B, the hollow tube 2 engages with a connector conduit 100 which in turn connects with the fusion cage 60 via a break-off collar 90. One or more connectors 102 connect the hollow tube 2 with the connector conduit 100. The hollow tube 2 fits over the connector conduit 100. The one or more connectors 102 fit through the hollow tube 2 and the connector conduit 100. The break-off collar 90 may be severed by any of several means, to include application of torsion and/or rotational force and/or lateral force to break-off collar 90, for example by twisting on the hollow tube 2 and/or the plunger 12. In one embodiment of the connector conduit 100, as shown in FIG. 17B, the connector conduit 100 is of circular cross-section.

A bone graft tamping device may also be provided, which is adapted to be telescopically inserted into the hollow tube after the plunger is removed from the hollow tube. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

The hollow tube may also be fitted with a passageway wherein a surgical tube or other device may be inserted, such as to deliver a liquid to the surgical area or to extract liquid from the surgical area. In such an embodiment, the plunger is adapted in cross-section to conform to the hollow tube's cross-section.

In another embodiment of the present invention, a kit of surgical instruments comprises a plurality of differently sized and/or shaped hollow tubes and a plurality of differently sized and/or shaped plungers. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectably delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

The kit of surgical instruments may comprise a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly may be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the integrated fusion cage and graft delivery device may either come with a pre-filled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger and hollow tube cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

According to the embodiment described in the preceding paragraph, the present invention may be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area and permits lateral or nearly lateral (n relation to the longitudinal axis of the hollow tube and plunger assembly) introduction of bone graft to the graft receiving area. This method prevents loss of bone graft due to improper or limited orientation of the integrated fusion cage and graft delivery device, and further allows a user to achieve insertion of a desired quantity of bone graft by way of the contoured plunger and hollow tube configuration described according to preferred embodiments herein.

The method of the present invention may also be carried out by providing a hollow tube having a first end and a second end, constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger in a generally downward direction through the hollow tube (i.e., in a direction from the first end to the second end). According to this embodiment, a graft retaining structure may also be provided for use in connection with the contoured edge of the plunger, such that the graft retaining structure is positioned between the contoured edge of the plunger and the bone graft, but which is adhered to the bone graft and remains at the graft receiving area following removal from the hollow tube. Furthermore, this graft retaining structure may also be employed with another tool, such as a graft packer, which is employed either before or after the hollow tube is removed from the graft receiving area.

In another embodiment, the one or more plungers corresponding to the one or more hollow tubes are positioned with distal ends near the proximate end of the horizontal tube before use, said plungers having a detent to retain plunger in ready position without undesired movement before surgeon chooses which one or more plungers to extend through hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design preferably comprises a hollow tubular member comprising a rounded edge rectangular shaft, which may be filled or is pre-filled with grafting material. The loading is carried out by the plunger. The rectangular design is preferable as it allows the largest surface area device to be placed into the annulotomy site of a disk, but in other embodiments may be formed similar to conventional round shafts. The other preferred feature includes a laterally-mounted exit site for the graft material. The combination of this design feature allows direction-oriented dispersion of the graft material. This allows ejection of the graft material into an empty disk space as opposed to below the hollow tube, which would tend to impact the material and not allow its spread through a disk space.

Another feature of this design is that a rectangular design allows the user to readily determine the orientation of the device and thereby the direction of entry of the bone graft material into the surgical area. However, such a feature may be obtained alternatively through exterior markings or grooves on the exterior on the hollow tube. Such exterior grooves or markings would allow use of a range of cross-sections for the device, to include a square, circle, or oval while allowing the user to readily determine the orientation of the device relative to the direction of entry of the bone graft material into the surgical area.

A further feature of this design is that an anti-perforation footing or shelf is paced on the bottom of the hollow tube to prevent annular penetration and/or injury to the patient's abdomen or other anatomy adjacent the bone graft receiving area.

Another alternative embodiment to the design described herein includes a removable funnel attachment. This allows easy loading of the cannula with the funnel and with its removal easy visualization of the operating site without visual blockage through the microscope.

In another embodiment of the invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alternative embodiment to the design described herein includes a navigation aid on one or more surfaces of the tubular body to permit surgeon to know how far the device has been inserted or to ensure proper alignment relative to a transverse bone graft delivery site (i.e. disc space). Such capability is particularly important when the patient or surgical area is not positioned immediately below the surgeon, or multiple procedures are being performed. A navigation aid allows more immediate and reliable locating of the surgical area for receiving of bone graft material. In one embodiment, the hollow tube is scored or marked or provides some affirmative indication, actively or passively, to the surgeon to indicate degree of delivery of the material, e.g. bone graft material, to the delivery site, and/or position of the plunger element. For example, the exterior of the hollow tube could be color-coded and/or provided with bars. In another embodiment, a computer and/or electro-mechanical sensor or device is used to provide feedback to the surgeon to indicate degree of delivery of the material, e.g. amount of cc's of bone graft material, to the delivery site, and/or position of the plunger element.

In another alternative embodiment to the design described herein, the plunger could include an activation device, which is often in a liquid or semi-liquid state, and that may be injected once the semi-solid portion of the morphogenic protein has been displaced by the movement of the plunger through the tubular body. That is, the plunger pushes the dry material, and once completed has a bulb or other device on the usable end to insert the liquid portion of the activating agent through the inner lumen within the plunger to evacuate the liquid from the plunger and out an opening at the non-usable end of the plunger so as to contact the dry material already inserted into the disc space)

To provide further clarity to the Detailed Description provided herein in the associated drawings, the following list of components and associated numbering are provided as follows:

REFERENCE NO. COMPONENT

1 Integrated fusion cage and graft delivery device
2 Hollow tube
4 Opening (of Hollow tube)
6 First end (of Hollow tube)
8 Second end (of Hollow tube)
10 Curved surface (of Hollow tube)
10A Curved interior surface (of Hollow tube)
11 Footing (of Hollow tube)
12 Plunger
16 Handle (of Plunger)
18 Second end (of Plunger)
19 Horizontal surface (of Plunger)
20 Curved surface (of Plunger)
30 Funnel
32 Sleeve (of Funnel)
34 Opening (of Funnel)
40 Disc space
A Height of opening (in Hollow tube)
B Width of opening (in Hollow tube)
50 Wedge-shaped Second end (of Hollow tube)
52 Wedge-shaped Second end (of Plunger)
60 Fusion Cage
62 Fusion Cage First End
64 Fusion Cage Second End
66 Fusion Cage First End Opening
68 Fusion Cage Medial Opening
69 Fusion Cage Lateral Opening
70 Fusion Cage Medial Surfaces
72 Fusion Cage Internal Ramps
80 Hollow Tube Locking Tabs
82 Fusion Cage Locking Slots
90 Break-off Collar
100 Connector Conduit
102 Connectors While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bone graft distribution apparatus comprising:
a hollow tube constructed to receive bone graft, said hollow tube having a length, an extended axis and a proximal end and a distal end, said hollow tube having a uniform interior cross-section from said proximal end to said distal end;
a substantially hollow implant detachably interconnected to the distal end of the hollow tube, said implant constructed to receive bone graft from said hollow tube, said implant having at least two openings having an upper and a lower end located on opposite lateral sides of said implant, said implant having a proximal end and a tapered distal end, said tapered distal end spanning the extended axis and forming the most distal end of the bone graft distribution apparatus, the implant proximal end forming a perimeter which engages the hollow tube distal end; and
a plunger adapted for inserting into said proximal end of said hollow tube along the extended axis, said plunger having a distal end exterior surface of cross-section contoured to said interior cross-section of said hollow tube, said plunger distal end exterior surface of cross-section forming a substantially congruent fit with said hollow tube uniform interior cross-section, said plunger having an axial length at least sufficient to extend to the length of the hollow tube;
wherein said hollow tube, said substantially hollow implant and said plunger are configured to deliver bone graft material into the interior of the substantially hollow implant and through the at least two openings of said substantially hollow implant when the plunger is advanced from the proximal end to the distal end of the hollow tube along the extended axis,
wherein the distal end of said plunger is configured to remain always proximal to the tapered distal end of said substantially hollow implant when said plunger is inserted into said hollow tube and said substantially hollow implant is attached to said hollow tube.

2. The apparatus according to claim 1, wherein said at least two openings are perpendicular to the longitudinal axis of said hollow tube.

3. The apparatus according to claim 1, wherein said implant comprises striations on a plurality of implant surfaces.

4. The apparatus according to claim 1, wherein said tapered distal end of said implant is wedge-shaped.

5. The apparatus according to claim 1, further comprising:
a detachable funnel adapted to connect to said proximal end of said hollow tube, wherein said detachable funnel facilitates insertion of bone graft into said hollow tube.

6. The apparatus of claim 1, wherein said plunger distal end comprises a substantially flat surface perpendicular to the extended axis.

7. The apparatus of claim 1, wherein said hollow tube, said implant and said plunger have substantially rectangular cross sectional shapes along an axis substantially perpendicular to said extended axis of said hollow tube.

8. The apparatus of claim 1, wherein said distal end of at least one of said plunger and said hollow tube are constructed of material more flexible than material comprising said proximal end of said hollow tube, whereby a risk of injury to a patient is reduced.

9. The apparatus of claim 1, wherein said hollow tube is preloaded with one of bone graft and bone morphogenic protein.

10. The apparatus of claim 1, wherein said implant has at least one opening permitting bone graft material to pass therethrough.

11. The apparatus of claim 1, wherein said implant is expendable.

12. The apparatus of claim 1, wherein said hollow tube has at least one telescoping portion to accommodate variation in said length of said hollow tube.

13. A bone graft distribution apparatus comprising:
a hollow tube constructed to receive bone graft, said hollow tube having a length, an extended axis and a proximal end and a distal end, said hollow tube having a uniform interior cross-section;
a substantially hollow implant detachably interconnected to the distal end of the hollow tube, said implant constructed to receive bone graft from said hollow tube, said implant having at least two symmetrical openings located opposite to one another, said implant having a proximal end and a distal end, said distal end spanning the extended axis and forming the most distal end of the bone graft distribution apparatus;
a plunger adapted for insertion within said hollow tube along the extended axis of said hollow tube, said plunger having an axial length at least sufficient to extend to the length of the hollow tube;
whereby said plunger is constructed and arranged with respect to said hollow tube so as to present at least one substantially flat contour;
whereby said plunger has a distal end exterior surface of cross-section contoured to said interior cross-section of said hollow tube, said plunger distal end exterior surface of cross-section forming a substantially congruent fit with said hollow tube uniform interior cross-section;

wherein said hollow tube, said substantially hollow implant and said plunger are configured to deliver bone graft material into the interior of the substantially hollow implant and through the at least two symmetrical openings of said substantially hollow implant when the plunger is advanced from the proximal end to the distal end of the hollow tube along the extended axis,
wherein the distal exterior tip of said plunger is configured to remain always proximal to the distal end of said substantially hollow implant when said plunger is inserted into said hollow tube and said substantially hollow implant is attached to said hollow tube.

14. The apparatus according to claim 13, wherein distal end of said implant is wedge-shaped.

15. The apparatus according to claim 13, further comprising:
communication between said proximal end of said hollow tube and said graft receiving area, wherein said communication is at least one of electrical and mechanical.

16. The apparatus according to claim 13, wherein said hollow tube, said implant and said plunger have substantially rectangular cross sectional shapes along an axis substantially perpendicular to said extended axis.

17. The apparatus according to claim 13, further comprising:
a detachable funnel positioned at said proximal end of said hollow tube, wherein said detachable funnel facilitates insertion of bone graft into said hollow tube.

18. The apparatus of claim 14, wherein said implant comprises striations on at least one implant surface.

19. A bone graft insertion apparatus for use by a user comprising:
a hollow tube constructed to receive bone graft, said hollow tube having an extended axis and a proximal end and a distal end, said hollow tube having a uniform interior cross-section from said proximal end to said distal end;
a substantially hollow implant detachably interconnected to the distal end of the hollow tube, said implant constructed to receive bone graft from said hollow tube, said implant having a proximal end and a distal end, said implant having a symmetrical shape about each of two planes along the extended axis, the implant proximal end forming a perimeter which engages the hollow tube distal end;
a plunger adapted for inserting into said proximal end of said hollow tube along the extended axis, said plunger having a distal end exterior surface of cross-section contoured to said interior cross-section of said hollow tube, said plunger distal end exterior surface of cross-section forming a substantially congruent fit with said hollow tube uniform interior cross-section;
wherein the bone graft insertion apparatus does not substantially obstruct the user's view of a graft receiving area;
wherein the insertion of the plunger into the hollow tube does not require a gun-type lever assembly; and
wherein said graft receiving area is configured to accommodate at least one substantially hollow implant.

20. The apparatus of claim 19, wherein said implant has at least one opening permitting bone graft material to pass therethrough.

* * * * *